(12) United States Patent
Feucht et al.

(10) Patent No.: US 7,115,543 B2
(45) Date of Patent: Oct. 3, 2006

(54) ARYL SULFONYL AMINO CARBONYL TRIAZOLE BASED SELECTIVE HERBICIDES

(75) Inventors: Dieter Feucht, Monheim (DE); Peter Dahmen, Neuss (DE); Mark Wilhelm Drewes, Langenfeld (DE); Rolf Pontzen, Leichlingen (DE); Mathias Kremer, Burscheid (DE); Klaus-Helmut Müller, Düsseldorf (DE)

(73) Assignee: Bayer CropScience AG, Monheim (DE)

( * ) Notice: Subject to any disclaimer, the term of this patent is extended or adjusted under 35 U.S.C. 154(b) by 56 days.

(21) Appl. No.: 10/312,151

(22) PCT Filed: Jun. 18, 2001

(86) PCT No.: PCT/EP01/06840

§ 371 (c)(1),
(2), (4) Date: Dec. 19, 2002

(87) PCT Pub. No.: WO02/01957

PCT Pub. Date: Jan. 10, 2002

(65) Prior Publication Data

US 2003/0211942 A1 Nov. 13, 2003

(30) Foreign Application Priority Data

Jun. 30, 2000 (DE) ......................... 100 31 825

(51) Int. Cl.
- *A01N 25/32* (2006.01)
- *A01N 43/653* (2006.01)
- *A01N 43/38* (2006.01)
- *A01N 43/30* (2006.01)
- *A01N 43/90* (2006.01)

(52) U.S. Cl. .................. 504/105; 504/106; 504/107; 504/129; 504/130; 504/132; 504/134; 504/135; 504/136; 504/137; 504/138; 504/139

(58) Field of Classification Search .............. 504/105, 504/106, 107, 129, 130, 132, 134, 135, 136, 504/137, 138, 139
See application file for complete search history.

(56) References Cited

U.S. PATENT DOCUMENTS

| | | | | |
|---|---|---|---|---|
| 4,623,727 A | 11/1986 | Hübele | ........................ | 546/178 |
| 4,639,266 A | 1/1987 | Heubach et al. | ................ | 71/92 |
| 4,758,264 A | 7/1988 | Hubele | .......................... | 71/94 |
| 4,785,105 A | 11/1988 | Hubele | ........................ | 546/178 |
| 4,785,106 A | 11/1988 | Hubele | ........................ | 546/178 |
| 4,822,884 A | 4/1989 | Hubele | ........................ | 546/177 |
| 4,851,033 A | 7/1989 | Hubele | .......................... | 71/94 |
| 4,881,966 A | 11/1989 | Nyffeler et al. | ................ | 71/94 |
| 4,891,057 A | 1/1990 | Sohn et al. | .................... | 71/72 |
| 4,902,340 A | 2/1990 | Hubele | .......................... | 71/94 |
| 5,023,333 A | 6/1991 | Hubele | ........................ | 546/175 |
| 5,045,107 A | 9/1991 | Hubele | .......................... | 71/94 |
| 5,057,144 A | 10/1991 | Daum et al. | .................... | 71/92 |
| 5,082,949 A | 1/1992 | Sohn et al. | ................. | 548/378 |
| 5,085,684 A | 2/1992 | Muller et al. | ................... | 71/92 |
| 5,094,683 A | 3/1992 | Daum et al. | .................... | 71/94 |
| 5,102,445 A | 4/1992 | Hubele | .......................... | 71/94 |
| 5,149,356 A | 9/1992 | Müller et al. | ................... | 71/90 |
| 5,238,910 A | 8/1993 | Müller et al. | ................ | 504/273 |
| 5,241,074 A | 8/1993 | Daum et al. | ............ | 548/263 B |
| 5,276,162 A | 1/1994 | Müller et al. | ............ | 548/263.4 |
| 5,314,863 A | 5/1994 | Löher et al. | ................ | 504/100 |
| 5,380,852 A | 1/1995 | Schütze et al. | .............. | 546/174 |
| 5,401,700 A | 3/1995 | Sohn et al. | ................. | 504/106 |
| 5,494,886 A | 2/1996 | Kehne et al. | ................ | 504/215 |
| 5,516,750 A | 5/1996 | Willms et al. | .............. | 504/106 |
| 5,529,976 A | 6/1996 | Kehne et al. | ................ | 504/213 |
| 5,534,486 A | 7/1996 | Müller et al. | ................ | 504/273 |
| 5,576,440 A | 11/1996 | Kehne et al. | ................ | 546/294 |
| 5,597,939 A | 1/1997 | Müller et al. | .................. | 558/8 |
| 5,635,451 A | 6/1997 | Kehne et al. | ................ | 504/215 |
| 5,700,758 A | 12/1997 | Rösch et al. | ................ | 504/106 |
| 5,703,008 A | 12/1997 | Rösch et al. | ................ | 504/106 |
| 5,739,079 A | 4/1998 | Holdgrün et al. | ............ | 504/103 |
| 5,869,681 A | 2/1999 | Müller et al. | ............ | 548/263.6 |
| 5,945,541 A | 8/1999 | Sohn et al. | .............. | 548/374.1 |
| 5,985,796 A | 11/1999 | Baltruschat et al. | ......... | 504/130 |
| 5,994,273 A | 11/1999 | Müller et al. | ................ | 504/273 |
| 6,121,204 A | 9/2000 | Müller et al. | ................ | 504/273 |
| 6,153,761 A | 11/2000 | Müller et al. | ............ | 548/263.6 |
| 6,251,831 B1 | 6/2001 | Müller et al. | ................ | 504/273 |
| 6,482,947 B1 | 11/2002 | Holdgrün et al. | ........... | 544/239 |
| 6,511,940 B1 * | 1/2003 | Ziemer et al. | .............. | 504/118 |
| 6,525,211 B1 | 2/2003 | Müller et al. | ................ | 558/413 |
| 6,821,926 B1 | 11/2004 | Feucht et al. | ............... | 504/128 |
| 2003/0060367 A1 | 3/2003 | Bieringer et al. | ........... | 504/133 |

FOREIGN PATENT DOCUMENTS

| | | | |
|---|---|---|---|
| CA | 2078811 | | 3/1993 |
| CA | 2258650 | | 2/1998 |
| DE | 199 15 013 | | 8/1999 |
| DE | 199 19 951 | | 9/1999 |
| EP | 0 346 620 | | 12/1989 |
| WO | 96/11188 | | 4/1996 |
| WO | 98/12923 | * | 4/1998 |
| WO | 99/37153 | * | 7/1999 |
| WO | 00/27203 | | 5/2000 |

OTHER PUBLICATIONS

Weeds, 15, (month unavailable) 1967, pp. 20–22, "Calculating Synergistic and Antagonistic Responses of Herbicide Combinations" by S. R. Colby.

* cited by examiner

Primary Examiner—S. Mark Clardy
(74) Attorney, Agent, or Firm—Richard E. L. Henderson; Raymond J. Harmuth

(57) ABSTRACT

The invention relates to novel herbicidal synergistic active compound combinations which comprise firstly arylsulphonylaminocarbonyltriazolinones and secondly herbicidally active compounds and/or safeners listed in the description, and which can be used with particularly good results for the selective control of weeds in various crops of useful plants.

6 Claims, No Drawings

ARYL SULFONYL AMINO CARBONYL TRIAZOLE BASED SELECTIVE HERBICIDES

The invention relates to novel herbicidal synergistic active compound combinations which comprise firstly known arylsulphonylaminocarbonyltriazolinones and secondly known herbicidally active compounds, and which can be used with particularly good results for the selective control of weeds in various crops of useful plants.

Arylsulphonylaminocarbonyltriazolinones, being broad-range herbicides, are the subject-matter of a series of patent applications (cf. EP-A-341489, EP-A-422469, EP-A-425948, EP-A-431291, EP-A-507171, EP-A-534266, WO-A-96/11188, WO-A-96/27590, WO-A-96/27591, WO-A-97/03056). However, under certain circumstances, the known sulphonylaminocarbonyltriazolinones still have gaps with regard to their action.

A number of herbicidal active compound combinations based on arylsulphonylaminocarbonyltriazolinones have also been disclosed already (cf. WO-A-98/12923). Again, however, the properties of these active compound combinations are not satisfactory in all respects.

Surprisingly, it has now been found that a number of known active compounds from the group of the arylsulphonylaminocarbonyltriazolinones, used jointly with known herbicidally active compounds from various classes of substances, show pronounced synergistic effects with regard to the action against weeds and can be employed particularly advantageously as broad-range combination products for the selective control of weeds in crops of useful plants such as, for example, barley, maize, rice and wheat.

The invention provides selective herbicidal compositions, characterized in that they comprise an effective amount of an active compound combination consisting of (a) an arylsulphonylaminocarbonyltriazolinone of the general formula (I)

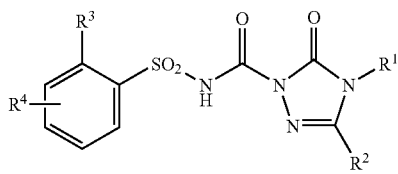

in which $R^1$ represents hydrogen, hydroxyl, amino, alkylideneamino or represents in each case optionally substituted alkyl, alkenyl, alkinyl, alkoxy, alkenyloxy, alkylamino, dialkylamino, cycloalkyl, cycloalkylalkyl, cycloalkylamino, aryl or arylalkyl, $R^2$ represents hydrogen, hydroxyl, mercapto, amino, cyano, halogen or represents in each case optionally substituted alkyl, alkoxy, alkylthio, alkylamino, dialkylamino, alkenyl, alkinyl, alkenyloxy, alkinyloxy, alkenylthio, alkinylthio, alkenylamino, alkinylamino, cycloalkyl, cycloalkyloxy, cycloalkylthio, cycloalkylamino, cycloalkylalkyl, aryl, aryloxy, arylthio, arylamino or arylalkyl, $R^3$ represents nitro, cyano, halogen or represents in each case optionally substituted alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkinyl, alkinyloxy, alkinylthio, cycloalkyl, cycloalkyloxy, cycloalkylthio, cycloalkylamino, aryl, aryloxy, arylthio, arylsulphinyl, arylsulphonyl or arylamino, and $R^4$ represents hydrogen, nitro, cyano, halogen or represents in each case optionally substituted alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkinyl, alkinyloxy, alkinylthio, cycloalkyl, cycloalkyloxy, cycloalkylthio, cycloalkylamino, aryl, aryloxy, arylthio, arylsulphinyl, arylsulphonyl or arylamino, and/or a salt of a compound of the formula (I) ("active compounds of group 1") and (b) one to three compounds from a second group of herbicides comprising the active compounds listed below:

5-(2-chloro-4-trifluoromethyl-phenoxy)-2-nitro-benzoic acid sodium salt (acifluorfen-sodium), 4-amino-N-(1,1-dimethyl-ethyl)-4,5-dihydro-3-(1-methyl-ethyl)-5-oxo-1H-1,2,4-triazole-1-carboxamide (amicarbazone), 1H-1,2,4-triazol-3-amine (amitrole), 2-[2,4-dichloro-5-(2-propinyloxy)-phenyl]-5,6,7,8-tetrahydro-1,2,4-triazolo-[4,3-a]-pyridin-3(2H)-one (azafenidin), N-(4,6-dimethoxy-pyrimidin-2-yl)-N'-[1-methyl-4-(2-methyl-2H-tetrazol-5-yl)-1H-pyrazol-5-ylsulphonyl]-urea (azimsulfuron), N-benzyl-2-(4-fluoro-3-trifluoromethyl-phenoxy)-butanamide (beflubutamid), N-butyl-N-ethyl-2,6-dinitro-4-trifluoromethyl-benzenamine (benfluralin), N-(4,6-dimethoxy-pyrimidin-2-yl)-N'-(2-methoxycarbonyl-phenylmethylsulphonyl)-urea (bensulfuron), methyl 2-[2-[4-(3,6-dihydro-3-methyl-2,6-dioxo-4-trifluoromethyl-1(2H)-pyrimidinyl)phenoxy]methyl]-5-ethyl-phenoxy-propanoate (benzfendizone), 3-(2-chloro-4-methylsulphonyl-benzoyl)-4-phenylthio-bicyclo-[3.2.1]-oct-3-en-2-one (benzobicyclon), [1,1-dimethyl-2-oxo-2-(2-propenyloxy) ]-ethyl 2-chloro-5-(3,6-dihydro-3-methyl-2,6-dioxo-4-trifluoromethyl-1(2H)-pyrimidinyl)-benzoate (butafenacil-allyl), 2-(1-ethoximino-propyl)-3-hydroxy-5-[2,4,6-trimethyl-3-(1-oxo-butyl)-phenyl]-2-cyclohexen-1-one (butroxydim), N,N-diethyl-3-(2,4,6-trimethyl-phenylsulphonyl)-1H-1,2,4-triazole-1-carboxamide (cafenstrole), 2-[1-[(3-chloro-2-propenyl)-oxy-imino]-propyl]-3-hydroxy-5-(tetrahydro-2H-pyran-4-yl)-2-cyclohexen-1-one (caloxydim, tepraloxydim), N-(4-chloro-6-methoxy-pyrimidin-2-yl)-N'-(2-ethoxycarbonyl-phenylsulphonyl)-urea (chlorimuron-ethyl), ethyl 2-chloro-3-[2-chloro-5-(1,3,4,5,6,7-hexahydro-1,3-dioxo-2H-isoindol-2-yl)-phenyl]-2-propanoate (cinidon-ethyl), 2-[1-[2-(4-chloro-phenoxy)-propoxyamino]butyl]-5-(tetrahydro-2H-thiopyran-3-yl)-1,3-cyclohexanedione (clefoxydim), (E,E)-(+)-2-[1-[[(3-chloro-2-propenyl)-oxy-]-imino]-propyl]-3-hydroxy-2-cyclohexen-1-one (clethodim), 2-(1-ethoximinobutyl)-3-hydroxy-5-(tetrahydro-2H-thiopyran-3-yl)-2-cyclohexen-1-one (cycloxydim), butyl (R)-2-[4-(4-cyano-2-fluoro-phenoxy)-phenoxy]-propanoate (cyhalofop-butyl), N-(2,6-dichloro-phenyl)-5-ethoxy-7-fluoro-[1,2,4]-triazolo-[1,5-c]-pyrimidine-2-sulphonamide (diclosulam), 2-[1-[(3,5-difluoro-phenyl)-amino-carbonyl-hydrazono]-ethyl]-pyridine-3-carboxylic acid (diflufenzopyr), S-(1-methyl-1-phenyl-ethyl) 1-piperidine-carbothioate (dimepiperate), (S-)-2-chloro-N-(2,4-dimethyl-3-thienyl)-N-(2-methoxy-1-methyl-ethyl)-acetamide (dimethenamid-P), 2-[2-(3-chloro-phenyl)-oxiranylmethyl]-2-ethyl-1H-indene-1,3(2H)-dione (epropodan), ethyl (R)-2-[4-(6-chloro-benzoxazol-2-yl-oxy)-phenoxy]-propanoate (fenoxaprop-(P)-ethyl), 4-(2-chloro-phenyl)-N-cyclohexyl-N-ethyl-4,5-dihydro-5-oxo-1H-tetrazole-1-carboxamide (fentrazamide), N-(2,6-difluoro-phenyl)-8-fluoro-5-methoxy-[1,2,4]-triazolo-[1,5-c]-pyrimidine-2-sulphonamide (florasulam), butyl (R)-2-[4-(5-trifluoromethyl-pyridin-2-yl-oxy)-phenoxy]-propanoate (fluazifop, -butyl, -P-butyl), i-propyl 5-(4-bromo-1-methyl-5-trifluoromethyl-1H-pyrazol-3-yl)-2-chloro-4-fluoro-benzoate (fluazolate), N-(4-fluorophenyl)-N-isopropyl-2-(5-trifluoromethyl-1,3,4-thiadiazol-2-yl-oxy)-acetamide (flufenacet), ethyl [2-chloro-4-fluoro-5-(5-methyl-6-oxo-4-trifluoromethyl-1(6H)-pyridazinyl)-phenoxy]-acetate (flufenpyr), 2-[7-fluoro-3,4-dihydro-3-oxo-4-(2-propinyl)-2H-1,4-benzoxazin-6-yl]-4,5,6,7-tetrahydro-1H-isoindole-1,3-dione (flumioxazin), 3-chloro-4-chloromethyl-1-(3-trifluoromethyl-phenyl)-2-pyrrolidinone (fluorochloridone), 5-(2-chloro-4-trifluoromethyl-phenoxy)-N-methylsulphonyl-2-nitro-benzamide (fomesafen), 2-[[[[(4,6-dimethoxy-2-pyrimidinyl)-amino ]-carbonyl]-amino]-sulphonyl]-4-formylamino-N,N-dimethyl-benzamide (foramsulfuron), (R)-2-[4-(3-chloro-5-trifluoromethyl-pyridin-2-yl-oxy)-phenoxy ]-propanoic acid (methyl ester, 2-ethoxy-ethyl ester, butyl ester) (haloxyfop, -methyl, -P-methyl, -ethoxyethyl, -butyl), N-(4-methoxy-6-methyl-1,3,5-triazin-2-yl)-N'-(5-iodo-2-methoxycarbonyl-phenylsulphonyl)-urea sodium salt (iodosulfuron-methyl-sodium), (4-chloro-2-methylsulphonyl-phenyl)-(5-cyclopropyl-isoxazol-4-yl)-methanone (isoxachlortole), (2-ethoxy-1-methyl-2-oxo-ethyl)-5-(2-chloro-4-trifluoromethyl-phenoxy)-2-nitro-benzoate (lactofen), 2-(2-benzothiazolyloxy)-N-methyl-N-phenyl-acetamide (mefenacet), methyl 2-[[[[(4,6-dimethoxy-2-pyrimidinyl)-amino ]-carbonyl]-amino]-sulphonyl]-4-[[(methylsulphonyl)-amino ]methyl]-benzoate (mesosulfuron), 2-(4-methylsulphonyl-2-nitro-benzoyl)-1,3-cyclohexanedione (mesotrione), 4-amino-3-methyl-6-phenyl-1,2,4-triazin-5(4H)-one (metamitron), (S)-2-chloro-N-(2-ethyl-6-methyl-phenyl)-N-(2-methoxy-1-methyl-ethyl)-acetamide (S-metolachlor), 4-dipropylamino-3,5-dinitro-benzenesulphonamide (oryzalin), 3-[2,4-dichloro-5-(2-propinyloxy)-phenyl]-5-(t-butyl)-1,3,4-oxadiazol-2(3H)-one (oxadiargyl), 3-[2,4-dichloro-5-(1-methyl-ethoxy)-phenyl]-5-(t-butyl)-1,3,4-oxadiazol-2(3H)-one (oxadiazon), 3-[1-(3,5-dichloro-phenyl)-1-i-propyl]-2,3-dihydro-6-methyl-5-phenyl-4H-1,3-oxazin-4-one (oxaziclomefone), 2-chloro-1-(3-ethoxy-4-nitro-phenoxy)-4-trifluoromethyl-benzene (oxyfluorfen), 2-(2,2-difluoro-ethoxy)-N-(5,8-dimethoxy[1,2,4]trizolo[1,5-c]pyrimidin-2-yl)-6-trifluoromethyl-benzenesulphonamide (penoxsulam), 2-chloro-N-(2-ethoxy-ethyl)-N-(2-methyl-1-phenyl-2-propenyl)-acetamide (pethoxamid), 1-chloro-N-[2-chloro-4-fluoro-5-[(6S,7aR)-6-fluoro-tetrahydro-1,3-dioxo-1H-pyrrolo[1,2-c]imidazol-2(3H)-yl]-phenyl ]-methanesulphonamide (profluazol), N-(3,4-dichloro-phenyl)-propanamide (propanil), (R)-2-[[(1-methyl-ethylidene)-amino]-oxy]-ethyl]-2-[4-(6-chloro-2-quinoxalinyloxy)-phenoxy ]-propanoate (propaquizafop), 2-chloro-N-(2-ethyl-6-methyl-phenyl)-N-[(1-methyl-ethoxy)-methyl]-acetamide (propisochlor), 1-(3-chloro-4,5,6,7-tetrahydropyrazolo[1,5-a]-pyridin-2-yl)-5-(methyl-2-propinylamino)-1H-pyrazole-4-carbonitrile (pyraclonil), 6-chloro-3-phenyl-4-pyridazin-4-ol (pyridatol), 7-[(4,6-dimethoxy-2-pyrimidinyl)-thio]-3-methyl-1(3H)-isobenzofuranone (pyriftalid), methyl 2-(4,6-dimethoxy-pyrimidin-2-yl-oxy)-benzoate (pyriminobac-methyl), 2-chloro-6-(4,6-dimethoxy-pyrimidin-2-ylthio)-benzoic acid sodium salt (pyrithiobac-sodium), 3,7-dichloro-quinoline-8-carboxylic acid (quinchlorac), 2-[4-(6-chloro-2-quinoxalinyloxy)-phenoxy]-propanoic acid (ethyl ester, tetrahydro-2-furanyl-methyl ester) (quizalofop, -ethyl, -P-ethyl, -P-tefuryl), 2-(1-ethoximinobutyl)-5-(2-ethylthiopropyl)-3-hydroxy-2-cyclohexen-1-one (sethoxydim), methyl 2-difluoromethyl-5-(4,5-dihydro-thiazol-2-yl)-4-(2-methyl-propyl)-6-trifluoromethyl-pyridine-3-carboxylate (thiazopyr), (3,5,6-trichloro)-pyridin-2-yl-oxy-acetic acid (triclopyr), N-[[(4,6-dimethoxy-2-pyrimidinyl)-amino]-carbonyl]-3-(2,2,2-trifluoro-ethoxy)-2-pyridinesulphonamide sodium salt (trifloxysulfuron), N-[4-dimethylamino-6-(2,2,2-trifluoro-ethoxy)-1,3,5-triazin-2-yl]-N'-(2-methoxycarbonyl-phenylsulphonyl)-urea (triflusulfuron-methyl), N-[[(4,6-dimethoxy-2-pyrimidinyl)-amino ]-carbonyl]-3-(N-methyl-N-methylsulphonyl-amino)-2-pyridinesulphonamide (cf. WO-A-92/10660), 2-(3,4-difluoro-phenoxy)-4-methyl-6-[(1-methyl-3-trifluoromethyl-1H-pyrazol-5-yl)-oxy]-pyridine (cf. EP-A-937397, WO-A-98/04548), ("active compounds of group 2"), and optionally (c) a compound which improves crop plant compatibility, from the group of compounds below:

4-dichloroacetyl-1-oxa-4-aza-spiro[4.5]-decane (AD-67), 1-dichloroacetyl-hexahydro-3,3,8a-trimethylpyrrolo[1,2-a]-pyrimidin-6(2H)-one (dicyclonon, BAS-145138), 4-dichloroacetyl-3,4-dihydro-3-methyl-2H-1,4-benzoxazine (benoxacor), 1-methyl-hexyl 5-chloro-quinolin-8-oxy-acetate (cloquintocet-mexyl—cf. also related compounds in EP-A-86750, EP-A-94349, EP-A-191736, EP-A-492366), 3-(2-chloro-benzyl)-1-(1-methyl-1-phenyl-ethyl)-urea (cumyluron), α-(cyanomethoximino)-phenylacetonitrile (cyometrinil), 2,4-dichloro-phenoxy acetic acid (2,4-D), 1-(1-methyl-1-phenyl-ethyl)-3-(4-methyl-phenyl)-urea (daimuron, dymron), 3,6-dichloro-2-methoxy-benzoic acid (dicamba), S-1-methyl-1-phenyl-ethyl piperidine-1-thiocarboxylate (dimepiperate), 2,2-dichloro-N-(2-oxo-2-(2-propenylamino)-ethyl)-N-(2-propenyl)-acetamide (DKA-24), 2,2-dichloro-N,N-di-2-propenyl acetamide (dichlormid), 4,6-dichloro-2-phenyl-pyrimidine (fenclorim), ethyl 1-(2,4-dichloro-phenyl)-5-trichloromethyl-1H-1,2,4-triazole-3-carboxylate (fenchlorazole-ethyl—cf. also related compounds in EP-A-174562 and EP-A-346620), phenylmethyl 2-chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole, MON-13900), ethyl-4,5-dihydro-5,5-diphenyl-3-isoxazole carboxylate (isoxadifen-ethyl—cf. also related compounds in WO-A-95/07897), diethyl-1-(2,4-dichloro-phenyl)-4,5-dihydro-5-methyl-1H-pyrazole-3,5-dicarboxylate (mefenpyr-diethyl—cf. also related compounds in WO-A-91/07874), 2-dichloromethyl-2-methyl-1,3-dioxolane (MG-191), 1,8-naphthalic anhydride, α-(1,3-dioxolan-2-yl-methoximino)-phenylacetonitrile (oxabetrinil), 2,2-dichloro-N-(1,3-dioxolan-2-yl-methyl)-N-(2-propenyl)-acetamide (PPG-1292), 3-dichloroacetyl-2,2-dimethyl-oxazolidine (R-28725), 3-dichloroacetyl-2,2,5-trimethyl-oxazolidine (R-29148), methyl 1-(2-chloro-phenyl)-5-phenyl-1H-pyrazole-3-carboxylate, ethyl 1-(2,4-dichloro-phenyl)-5-methyl-1H-pyrazole-3-carboxylate, ethyl 1-(2,4-dichloro-phenyl)-5-isopropyl-1H-pyrazole-3-carboxylate, ethyl 1-(2,4-dichloro-phenyl)-5-(1,1-dimethyl-ethyl)-1H-pyrazole-3-carboxylate, ethyl 1-(2,4-dichloro-phenyl)-5-phenyl-1H-pyrazole-3-carboxylate (cf. also related compounds in EP-A-269806 and EP-A-333131), ethyl 5-(2,4-dichloro-benzyl)-2-isoxazoline-3-carboxylate, ethyl 5-phenyl-2-isoxazoline-3-carboxylate, ethyl 5-(4-fluoro-phenyl)-5-phenyl-2-isoxazoline-3-carboxylate (cf. also related compounds in WO-A-91/08202), 1,3-dimethyl-but-1-yl 5-chloro-quinolin-8-oxy-acetate, 4-allyloxy-butyl 5-chloro-quinolin-8-oxy-acetate, 1-allyloxy-prop-2-yl 5-chloro-quinolin-8-oxy-acetate, methyl 5-chloro-quinolin-8-oxy-acetate, ethyl 5-chloro-quninolin-8-oxy-acetate, allyl 5-chloro-quinolin-8-oxy-acetate, 2-oxo-prop-1-yl 5-chloro-quinolin-8-oxy-acetate, diethyl 5-chloro-quinolin-8-oxy-malonate, diallyl 5-chloro-quinolin-8-oxy-malonate, diethyl 5-chloro-quinolin-8-oxy-malonate (cf. also related compounds in EP-A-582198), 2-(4-carboxy-chroman-4-yl)-acetic acid, 3,3'-dimethyl-4-methoxy-benzophenone, 1-bromo-4-chloromethylsulphonyl-benzene, N-(2-methoxy-benzoyl)-4-[(methylamino-carbonyl)-amino]-benzenesulphonamide, N-(2-methoxy-5-methyl-benzoyl)-4-(cyclopropylaminocarbonyl)-benzenesulphonamide, N-cyclopropyl-4-[(2-methoxy-5-methyl-benzoyl)-aminosulphonyl ]-benzamide (cf. WO 99/66795), ("active compounds of group 3").

Preferred meanings of the radicals listed in formula (I) shown above are illustrated below.

$R^1$ preferably represents hydrogen, hydroxyl, amino, $C_2$–$C_6$-alkylideneamino, represents in each case optionally cyano-, halogen- or $C_1$–$C_4$-alkoxy-substituted alkyl, alkenyl, alkinyl, alkoxy, alkenyloxy, alkylamino or dialkylamino having in each case up to 6 carbon atoms, represents in each case optionally cyano-, halogen- or $C_1$–$C_4$-alkyl-substituted cycloalkyl, cycloalkylalkyl or cycloalkylamino having in each case 3 to 6 carbon atoms in the cycloalkyl groups and optionally 1 to 4 carbon atoms in the alkyl moiety, or represents in each case optionally cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl or phenyl-$C_1$–$C_4$-alkyl.

$R^2$ preferably represents hydrogen, hydroxyl, mercapto, amino, cyano, halogen, represents in each case optionally cyano-, halogen- or $C_1$–$C_4$-alkoxy-substituted alkyl, alkoxy, alkylthio, alkylamino, dialkylamino, alkenyl, alkinyl, alkenyloxy, alkinyloxy, alkenylthio, alkinylthio, alkenylamino or alkinylamino having in each case up to 6 carbon atoms, represents in each case optionally cyano-, halogen- or $C_1$–$C_4$-alkyl-substituted cycloalkyl, cycloalkyloxy, cycloalkylthio, cycloalkylamino or cycloalkylalkyl having in each case 3 to 6 carbon atoms in the cycloalkyl groups and optionally 1 to 4 carbon atoms in the alkyl moiety, or represents in each case optionally cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy, phenylthio, phenylamino or phenyl-$C_1$–$C_4$-alkyl.

$R^3$ preferably represents nitro, cyano, halogen, represents in each case optionally cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkinyl, alkinyloxy, alkinylthio having in each case up to 6 carbon atoms, represents in each case optionally cyano-, halogen- or $C_1$–$C_4$-alkyl-substituted cycloalkyl, cycloalkyloxy, cycloalkylthio, cycloalkylamino having in each case 3 to 6 carbon atoms in the cycloalkyl groups, or represents in each case optionally cyano-, nitro-, halogen-, $C_1$–$C_4$-alkyl-, $C_1$–$C_4$-halogenoalkyl-, $C_1$–$C_4$-alkoxy-or $C_1$–$C_4$-halogenoalkoxy-substituted phenyl, phenoxy, phenylthio, phenylsulphinyl, phenylsulphonyl or phenylamino.

$R^4$ preferably represents hydrogen, nitro, cyano, halogen, represents in each case optionally cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, alkenyl, alkenyloxy, alkenylthio, alkenylamino, alkinyl, alkinyloxy or alkinylthio having in each case up to 6 carbon atoms, represents in each case optionally cyano-, halogen- or $C_1$–$C_4$-alkyl-substituted cycloalkyl, cycloalkyloxy, cycloalkylthio, cycloalkylamino having in each case 3 to 6 carbon atoms in the cycloalkyl groups, or represents in each case optionally cyano-, nitro-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted phenyl, phenoxy, phenylthio, phenylsulphinyl, phenylsulphonyl or phenylamino.

$R^1$ particularly preferably represents hydrogen, amino, represents in each case optionally cyano-, fluorine-, chlorine-, methoxy- or ethoxy-substituted methyl, ethyl, n- or i-propyl, n-, i-, s- or t-butyl, ethenyl, propenyl, butenyl, ethinyl, propinyl, butinyl, methoxy, ethoxy, n- or i-propoxy, n-, i-, s- or t-butoxy, propenyloxy, butenyloxy, methylamino, ethylamino, n- or i-propylamino, n-, i-, s- or t-butylamino, dimethylamino or diethylamino, represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropylmethyl, cyclobutylmethyl, cyclopentylmethyl, cyclohexylmethyl, cyclopropylamino, cyclobutylamino, cyclopentylamino or cyclohexylamino, or represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, difluoromethoxy- or trifluoromethoxy-substituted phenyl or benzyl.

$R^2$ particularly preferably represents hydrogen, hydroxyl, mercapto, amino, cyano, fluorine, chlorine, bromine, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino, diethylamino, ethenyl, propenyl, butenyl, ethinyl, propinyl, butinyl, propenyloxy, butenyloxy, propinyloxy, butinyloxy, propenylthio, butenylthio, propinylthio, butinylthio, propenylamino, butenylamino, propinylamino or butinylamino, represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl or cyclohexylmethyl, or represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, difluoromethoxy- or trifluoromethoxy-substituted phenyl, phenoxy, phenylthio, phenylamino or benzyl.

$R^3$ particularly preferably represents nitro, cyano, fluorine, chlorine, bromine, represents in each case optionally cyano-, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, ethenyl, propenyl, butenyl, propenyloxy, butenyloxy, propenylthio, butenylthio, propenylamino, butenylamino, ethinyl, propinyl, butinyl, propinyloxy, butinyloxy, propinyl-thio or butinylthio, represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, or represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenoxy, phenylthio, phenylsulphinyl, phenylsulphonyl or phenylamino.

$R^4$ particularly preferably represents hydrogen, nitro, cyano, fluorine, chlorine, bromine, represents in each case optionally cyano-, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, ethenyl, propenyl, butenyl, propenyloxy, butenyloxy, propenylthio, butenylthio, propenylamino, butenylamino, ethinyl, propinyl, butinyl, propinyloxy, butinyloxy, propinylthio or butinylthio, represents in each case optionally cyano-, fluorine-, chlorine-, bromine-, methyl-, ethyl-, n- or i-propyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, or represents in each case optionally cyano-, nitro-, fluorine-, chlorine-, bromine-, methyl-, ethyl-, n- or i-propyl-, trifluoromethyl-, methoxy-, ethoxy-, n- or i-propoxy-, n-, i-, s- or t-butoxy-, difluoromethoxy- or trifluoromethoxy-substituted phenyl, phenoxy, phenylthio, phenylsulphinyl, phenylsulphonyl or phenylamino.

$R^1$ very particularly preferably represents hydrogen, amino, represents in each case optionally fluorine-, chlorine-, methoxy- or ethoxy-substituted methyl, ethyl, n- or i-propyl, ethenyl, propenyl, ethinyl, propinyl, methoxy, ethoxy, methylamino or ethylamino, represents dimethylamino, or represents in each case optionally fluorine-, chlorine- or methyl-substituted cyclopropyl.

$R^2$ very particularly preferably represents hydrogen, chlorine, bromine, represents in each case optionally fluorine-, chlorine-, methoxy- or ethoxy-substituted methyl, ethyl, n- or i-propyl, n-, i- or s-butyl, methoxy, ethoxy, n- or i-propoxy, methylthio, ethylthio, n- or i-propylthio, methylamino, ethylamino, n- or i-propylamino, dimethylamino, diethylamino, ethenyl, propenyl, butenyl, ethinyl, propinyl, butinyl, propenyloxy, butenyloxy, propinyloxy, butinyloxy, propenylthio, butenylthio, propinylthio, butinylthio, propenylamino, butenylamino, propinylamino or butinylamino, or represents in each case optionally fluorine-, chlorine- or methyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino, cyclohexylamino, cyclopropylmethyl, cyclobutylmethyl, cyclopentylmethyl or cyclohexylmethyl.

$R^3$ very particularly preferably represents nitro, cyano, fluorine, chlorine, bromine, represents in each case optionally fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl, represents in each case optionally fluorine-, chlorine- or methyl-substituted cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio or cyclohexylthio, or represents in each case optionally cyano-, nitro-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- or trifluoromethoxy-substituted phenyl, phenoxy, phenylthio, phenylsulphinyl or phenylsulphonyl.

$R^4$ very particularly preferably represents hydrogen, nitro, cyano, fluorine, chlorine, bromine, or represents in each case optionally fluorine-, chlorine-, methoxy- or ethoxy-substituted methyl, ethyl, n- or i-propyl, methoxy, ethoxy, n- or i-propoxy, methoxycarbonyl, ethoxycarbonyl, n- or i-propoxycarbonyl, methylthio, ethylthio, n- or i-propylthio, methylsulphinyl, ethylsulphinyl, methylsulphonyl or ethylsulphonyl.

In place of the pure active compounds of the formula (I), it is also possible to use salts of the compounds of the formula (1) with metals and/or with basic nitrogen compounds in the active compound combinations according to the invention.

Preference is given here to salts of the compounds of the formula (I) with alkali metals, such as, for example, lithium, sodium, potassium, rubidium or caesium, very particularly preferably with sodium or potassium, with alkaline earth metals, such as, for example, magnesium, calcium or barium, very particularly preferably with calcium, or with earth metals, such as, for example, aluminium.

Preference is furthermore given to salts of the compounds of the formula (I) with ammonia, with $C_1$–$C_6$-alkyl-amines, such as, for example, with methylamine, ethylamine, n- or i-propylamine, n-, i-, s- or t-butylamine, n-, i-, s- or t-pentylamine, with di-($C_1$–$C_6$-alkyl)-amines, such as, for example, dimethylamine, diethylamine, dipropylamine, diisopropylamine, dibutylamine, diisobutylamine, di-s-butylamine, dipentylamine, diisopentylamine, di-s-pentylamine and dihexylamine, with tri-($C_1$–$C_4$-alkyl)-amines, such as, for example, trimethylamine, triethylamine, tripropylamine, tributylamine and N-ethyl-diisopropylamine, with $C_3$–$C_6$-cycloalkyl-amines, such as, for example, cyclopentylamine or cyclohexylamine, with di-($C_3$–$C_6$-cycloalkyl)-amines, such as, for example, dicyclopentylamine or dicyclohexylamine, with N-$C_1$–$C_4$-alkyl-$C_3$–$C_6$-cycloalkylamines, such as, for example, N-methyl-cyclopentylamine, N-ethyl-cyclopentylamine, N-methyl-cyclohexylamine or N-ethyl-cyclohexylamine, with N,N-di- ($C_1$–$C_4$-alkyl)-$C_3$–$C_6$-cycloalkyl-amines, such as, for example, N,N-dimethyl-cyclopentylamine, N,N-diethyl-cyclopentylamine, N,N-dimethyl-cyclohexylamine or N,N-diethyl-cyclohexylamine, with N-$C_1$–$C_4$-alkyl-di-($C_3$–$C_6$-cycloalkyl)-amines, such as, for example, N-methyl-dicyclopentylamine, N-ethyl-dicyclopentylamine, N-methyl-dicyclohexylamine or N-ethyl-dicyclohexylamine, with phenyl-$C_1$–$C_4$-alkyl-amines, such as, for example, benzylamine, 1-phenyl-ethylamine or 2-phenyl-ethylamine, with N-$C_1$–$C_4$-alkyl-phenyl-$C_1$–$C_4$-alkyl-amines, such as, for example, N-methyl-benzylamine or N-ethyl-benzylamine, or with N,N-di-($C_1$–$C_4$-alkyl)-phenyl-$C_1$–$C_4$-alkyl-amines, such as, for example, N,N-dimethyl-benzylamine or N,N-diethyl-benzylamine, or with optionally fused and/or $C_1$–$C_4$-alkyl-substituted azines, such as, for example, pyridine, quinoline, 2-methyl-pyridine, 3-methyl-pyridine, 4-methyl-pyridine, 2,4-dimethyl-pyridine, 2,5-dimethyl-pyridine, 2,6-dimethyl-pyridine or 5-ethyl-2-methyl-pyridine.

Basic compounds which may be mentioned as being suitable for preparing the salts of the compounds of the formula (I) that can be used according to the invention are: alkali metal or alkaline earth metal acetates, amides, carbonates, bicarbonates, hydrides, hydroxides or alkamolates, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide.

Examples which may be mentioned for the compounds of the formula (I) to be used as mixing partners according to the invention are:

2-(2-chloro-phenylsulphonylaminocarbonyl)-, 2-(2-bromo-phenylsulphonylaminocarbonyl)-, 2-(2-methyl-phenylsulphonylaminocarbonyl)-, 2-(2-ethyl-phenylsulphonylaminocarbonyl)-, 2-(2-n-propyl-phenylsulphonylaminocarbonyl)-, 2-(2-i-propyl-phenylsulphonylaminocarbonyl)-, 2-(2-trifluoromethyl-phenylsulphonylaminocarbonyl)-, 2-(2-methoxy-phenylsulphonylaminocarbonyl)-, 2-(2-ethoxy-phenylsulphonylaminocarbonyl)-, 2-(2-n-propoxy-phenylsulphonylaminocarbonyl)-, 2-(2-i-propoxy-phenylsulphonylaminocarbonyl)-, 2-(2-difluoromethoxy-phenylsulphonylaminocarbonyl)-, 2-(2-trifluoromethoxy-phenylsulphonylaminocarbonyl)-, 2-(2-methoxycarbonyl-phenylsulphonylaminocarbonyl)-, 2-(2-ethoxycarbonyl-phenylsulphonylaminocarbonyl)-, 2-(2-n-propoxycarbonyl-phenylsulphonylaminocarbonyl)-, 2-(2-i-propoxycarbonyl-phenylsulphonylaminocarbonyl)- and 2-(2-chloro-6-methyl-phenylsulphonylaminocarbonyl)-4-methyl-5-methoxy-2,4-dihydro-3H-1,2,4-triazol-3-one, -4-methyl-5-ethoxy-2,4-dihydro-3H-1,2,4-triazol-3-one, -4-methyl-5-n-propoxy-2,4-dihydro-3H-1,2,4-triazol-3-one, -4-methyl-5-i-propoxy-2,4-dihydro-3H-1,2,4-triazol-3-one, -4-methyl-5-trifluoroethoxy-2,4-dihydro-3H-1,2,4-triazol-3-one, -4-methyl-5-methylthio-2,4-dihydro-3H-1,2,4-triazol-3-one, -4-methyl-5-ethylthio-2,4-dihydro-3 H-1,2,4-triazol-3-one -4-methoxy-5-methyl-2,4-dihydro-3H-1,2,4-triazol-3-one, -4-methoxy-5-ethyl-2,4-dihydro-3H-1,2,4-triazol-3-one, -4-methoxy-5-n-propyl-2,4-dihydro-3H-1,2,4-triazol-3-one, -4-cyclopropyl-5-methoxy-2,4-dihydro-3H-1,2,4-triazol-3-one, -4-cyclopropyl-5-ethoxy-2,4-dihydro-3H-1,2,4-triazol-3-one, -4-cyclopropyl-5-n-propoxy-2,4-dihydro-3H-1,2,4-triazol-3-one, -4-cyclopropyl-5-i-propoxy-2,4-dihydro-3H-1,2,4-triazol-3-one and -4-cyclopropyl-5-trifluoroethoxy-2,4-dihydro-3H-1,2,4-triazol-3-one and the sodium and potassium salts of these compounds.

The compounds 2-(2-methoxycarbonyl-phenylsulphonylaminocarbonyl)-4-methyl-5-n-propoxy-2,4-dihydro-3H-1,2,4-triazol-3-one (I-1, procarbazone or propoxycarbazone) and 2-(2-trifluoromethoxy-phenylsulphonylaminocarbonyl)-4-methyl-5-methoxy-2,4-dihydro-3H-1,2,4-triazol-3-one (I-2, flucarbazone) and their sodium salts—(I-1-Na salt, procarbazone-sodium or propoxycarbazone-sodium), (I-2-Na salt, flucarbazone-sodium)—may be particularly emphasized as mixing components of the formula (I).

The compounds of the formula (I) are described in the patent applications and patents mentioned above.

According to their chemical structure, the active compounds of group 2 can be assigned to the following classes of active compounds:

amides (for example beflubutamid, propanil), arylheterocycles (for example azafenidin, benzfendizone, butafenacil-allyl, cinidon-ethyl, fluazolate, flumioxazin, oxadiazon, oxadiargyl, profluazol, pyraflufen-ethyl, pyridatol, 4-[4,5-dihydro-4-methyl-5-oxo-(3-trifluoromethyl)-1H-1,2,4-triazol-1-yl]-2-[(ethylsulphonyl)amino]-5-fluoro-benzenecarbothioamide), aryloxyphenoxypropionates (for example cyhalofop-butyl, fenoxaprop-P-ethyl, fluazifop-P-butyl, haloxyfop-P-methyl, quizalofop-P-ethyl), carboxylic acid derivatives (for example triclopyr), chloroacetamides (for example dimethenamid-P, S-metolachlor, propisochlor), cyclohexanediones (for example butroxydim, clefoxydim, cycloxydim, sethoxydim), dinitroanilines (for example benfluralin, oryzalin), diphenyl ethers (for example acifluorfen-sodium, fomesafen, lactofen, oxyfluorfen), isoxazoles (for example isoxachlortole), oxyacetamides (for example mefenacet), pyridines (for example thiazopyr), pyrimidinyl(thio)benzoates (for example pyribenzoxim, pyriminobac-methyl, pyrithiobac-sodium), sulphonylureas (for example azimsulfuron, bensulfuron, chloroimuron-ethyl, foramsulfuron, iodosulfuron-methyl-sodium, trifloxysulfuron, triflusulfuron-methyl), tetrazolinones (for example fentrazamide), thiocarbamates (for example dimepiperate), triazinones (for example metamitron), triazoles (for example amitrole), triazolopyrimidines (for example diclosulam, florasulam), triketones (for example mesotrione).

The following may be particularly emphasized as mixing components from amongst the active compounds of group 2:

amicarbazone, beflubutamid, cinidon-ethyl, fenoxaprop-P-ethyl, florasulam, fluazolate, flufenacet, iodosulfuron-methyl-sodium.

From this group, amicarbazone is a mixing component of very particular interest.

From this group, beflubutamid is a further mixing component of very particular interest.

From this group, cinidon-ethyl is a further mixing component of very particular interest.

From this group, fenoxaprop-P-ethyl is a further mixing component of very particular interest.

From this group, florasulam is a further mixing component of very particular interest.

From this group, fluazolate is a further mixing component of very particular interest.

From this group, flufenacet is a further mixing component of very particular interest.

From this group, iodosulfuron-methyl-sodium is a mixing component of very particular interest.

The compositions according to the invention preferably comprise one or two active compounds of group 1, one to three active compounds of group 2 and optionally one active compound of group 3.

The compositions according to the invention comprise in particular one active compound of group 1, one or two active compounds of group 2 and optionally one active compound of group 3.

The following may be particularly emphasized as mixing components from among the active compounds of group 3:

1-methyl-hexyl 5-chloro-quinolin-8-oxy-acetate (cloquintocet-mexyl) and diethyl1-(2,4-dichloro-phenyl)-4,5-dihydro-5-methyl-1H-pyrazole-3,5-dicarboxylate (mefenpyr-diethyl) for improving the compatibility in cereals.

Examples of the active compound combinations according to the invention which may be mentioned are:

flucarbazone-sodium+beflubutamid, flucarbazone-sodium+beflubutamid+mefenpyr-diethyl, flucarbazone-sodium+beflubutamid+cloquintocet-mexyl, flucarbazone-sodium+cinidon-ethyl, flucarbazone-sodium+cinidon-ethyl+mefenpyr-diethyl, flucarbazone-sodium+cinidon-ethyl+cloquintocet-mexyl, flucarbazone-sodium+fenoxaprop-P-ethyl, flucarbazone-sodium+fenoxaprop-P-ethyl+mefenpyr-diethyl, flucarbazone-sodium+fenoxaprop-P-ethyl+cloquintocet-mexyl, flucarbazone-sodium+florasulam, flucarbazone-sodium+florasulam+mefenpyr-diethyl, flucarbazone-sodium+florasulam+cloquintocet-mexyl, flucarbazone-sodium+flufenacet, flucarbazone-sodium+flufenacet+mefenpyr-diethyl, flucarbazone-sodium+flufenacet+cloquintocet-mexyl, flucarbazone-sodium+iodosulfuron-methyl-sodium, flucarbazone-sodium+iodosulfuron-methyl-sodium+mefenpyr-diethyl, flucarbazone-sodium+iodosulfuron-methyl-sodium+cloquintocet-mexyl.

Procarbazone-sodium+beflubutamid, procarbazone-sodium+beflubutamid+mefenpyr-diethyl, procarbazone-sodium+beflubutamid+cloquintocet-mexyl, procarbazone-sodium+cinidon-ethyl, procarbazone-sodium+cinidon-ethyl+mefenpyr-diethyl, procarbazone-sodium+cinidon-ethyl+cloquintocet-mexyl, procarbazone-sodium+fenoxaprop-P-ethyl, procarbazone-sodium+fenoxaprop-P-ethyl+mefenpyr-diethyl, procarbazone-sodium+fenoxaprop-P-ethyl+cloquintocet-mexyl, procarbazone-sodium+florasulam, procarbazone-sodium+florasulam+mefenpyr-diethyl, procarbazone-sodium+florasulam+cloquintocet-mexyl, procarbazone+iodosulfuron-methyl-sodium, procarbazone+iodosulfuron-methyl-sodium+mefenpyr-diethyl, procarbazone+iodosulfuron-methyl-sodium+cloquintocet-mexyl.

Surprisingly, it has now been found that the above-defined active compound combinations of the arylsulphonylaminocarbonyltriazolinones of the formula (I) and the abovementioned active compounds of group 2 exhibit a particularly high herbicidal activity combined with very good useful plant compatibility and can be used for the selective control of monocotyledonous and dicotyledonous weeds in a variety of crops, in particular in wheat, but also in barley, and also for controlling monocotyledonous and dicotyledonous weeds in the semi- and non-selective field. Surprisingly, the herbicidal activity of the active compound combinations according to the invention of compounds of the abovementioned groups 1 and 2 considerably exceeds the total of the actions of the individual active compounds.

Thus, not just a complementation of action but a synergistic effect is present which could not have been predicted.

The novel active compound combinations are well tolerated in a variety of crops, also effecting good control of weeds which are usually difficult to control. Thus, the novel active compound combinations are a valuable addition to the herbicides.

The synergistic effect of the active compound combinations according to the invention is particularly strongly pronounced in certain concentration ratios. However, the weight ratios of the active compounds in the active compound combinations may be varied within relatively wide ranges. In general, from 0.01 to 1000 parts by weight, preferably from 0.02 to 500 parts by weight and particularly preferably from 0.05 to 100 parts by weight of active compound of group 2 are used per part by weight of active compound of the formula (I).

The following may be particularly emphasized as mixing components from amongst the active compounds of group 3:

1-methyl-hexyl 5-chloro-quinolin-8-oxy-acetate (cloquintocet-mexyl), ethyl 4,5-dihydro-5,5-diphenyl-3-isoxazolecarboxylate (isoxadifen-ethyl) and diethyl 1-(2,4-dichloro-phenyl)-4,5-dihydro-5-methyl-1H-pyrazole-3,5-dicarboxylate (mefenpyr-diethyl) for improving the compatibility in cereals, and 4-dichloroacetyl-1-oxa-4-aza-spiro[4.5]-decane (AD-67), 1-dichloroacetyl-hexahydro-3,3,8a-trimethylpyrrolo[1,2-a ]-pyrimidin-6(2H)-one (BAS-145138), 4-dichloroacetyl-3,4-dihydro-3-methyl-2H-1,4-benzoxazine (benoxacor), 2,2-dichloro-N,N-di-2-propenyl-acetamide (dichlormid), 3-dichloroacetyl-2,2,5-trimethyl-oxazolidine (R-29148) and ethyl 1-(2,4-dichloro-phenyl)-5-trichloromethyl-1H-1,2,4-triazole-3-carboxylate (fenchlorazole-ethyl) for improving the compatibility in maize.

It must be considered as surprising that, from amongst a large number of known safeners or antidotes capable of antagonizing the harmful effect of a herbicide on the crop plants, it is precisely the abovementioned compounds of group 3 which are capable of almost completely neutralizing the harmful effect, on the crop plants, of active compounds of the formula (I) and their salts, if appropriate also in combination with one or more of the abovementioned active compounds of group 2, without adversely affecting the herbicidal efficacy towards the weeds.

The advantageous effect of the crop plant compatibility of the active compound combinations according to the invention is likewise particularly strongly pronounced at certain concentration ratios. However, the weight ratios of the active compounds in the active compound combinations can be varied within relatively wide ranges. In general, from 0.001 to 1000 parts by weight, preferably from 0.01 to 100 parts by weight and particularly preferably from 0.1 to 10 parts by weight of active compound of group 3 are used per part by weight of active compound of the formula (I) or its mixtures with active compounds of group 2.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant varieties protectable or not protectable by plant breeders' rights. Plant parts are to be understood as meaning all aerial and subterranean plant parts and organs of the plants such as shoot, leaf, flower and root, examples which may be mentioned being leaves, needles, stalks, trunks, flowers, fruiting bodies, fruits, seeds, roots, tubers and rhizomes. The plant parts also include vegetative and generative propagation material, for example cuttings, tubers, rhizomes, seedlings and seeds.

The treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on and, in the case of propagation material, in particular in the case of seeds, also by applying one or more coats.

Amongst the plants obtained by biotechnological and recombinant methods, or by combining these methods, plants which are emphasized are those which tolerate so-called 4-HPPD, EPSP and/or PPO inhibitors, such as, for example, Acuron plants.

The active compounds according to the invention can be used, for example, in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the genera: *Allium, Ananas, Asparagus, Avena, Hordeum, Oryza, Panicum, Saccharum, Secale, Sorghum, Triticale, Triticum, Zea.*

However, the use of the active compound combinations according to the invention is in no way restricted to these genera, but also extends in the same manner to other plants.

The active compound combinations to be used in accordance with the invention can be employed not only in conventional cultivation methods (suitably spaced row crops), in plantation crops (for example grapevines, fruit, citrus) and in industrial plants and railtracks, on paths and squares, but also for stubble treatment and in the minimum tillage method. They are furthermore suitable as dessicants (haulm killing in, for example, potatoes) or as defoliants (for example in cotton). They are furthermore suitable for use on non-crop areas. Other fields of application are nurseries, forests, grassland and the production of ornamentals.

The active compound combinations can be converted into the customary formulations such as solutions, emulsions, wettable powders, suspensions, powders, dusts, pastes, soluble powders, granules, suspo-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants and/or foam formers.

In the case of the use of water as an extender, organic solvents can, for example, also be used as cosolvents. The following are essentially suitable as liquid solvents: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Solid carriers which are suitable are:

for example ammonium salts and ground natural minerals such as kaolins, clays, talc, chalk, quartz, attapulgite, montmorillonite or diatomaceous earth, and ground synthetic materials such as highly-dispersed silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compounds, preferably between 0.5 and 90%.

The active compound combinations according to the invention are generally applied in the form of ready mixes. However, the active compounds contained in the active compound combinations may also be applied in the form of individual formulations which are mixed upon use, that is, in the form of tank mixes.

The novel active compound combinations, as such or in their formulations, may furthermore also be used as a mixture with other known herbicides, again with ready mixes or tank mixes being possible. A mixture with other known active compounds such as fungicides, insecticides, acaricides, nematicides, bird repellants, growth substances, plant nutrients and soil conditioners is also possible. It may furthermore be advantageous for specific applications, in particular for the post-emergence method, to incorporate into the formulations plant-tolerated mineral or vegetable oils (for example the commercial product "Oleo DuPont 11E") or ammonium salts such as, for example, ammonium sulphate or ammonium thiocyanate, as further additives.

The novel active compound combinations can be used as such, in the form of their formulations or the use forms prepared from these formulations by further dilution, such as ready-to-use solutions, suspensions, emulsions, powders, pastes and granules. Application is effected in the customary manner, for example by pouring, spraying, atomizing, dusting or broadcasting.

The active compound combinations according to the invention can be applied before and after emergence of the plants, that is to say by the pre- and post-emergence method. They may also be incorporated into the soil prior to sowing.

The good herbicidal action of the novel active compound combinations can be seen from the examples which follow. While the individual active compounds show weaknesses with regard to their herbicidal action, the combinations all show a very good herbicidal action which exceeds a simple sum of actions.

A synergistic effect in herbicides is always present when the herbicidal action of the active compound combination exceeds the action of the active compounds when applied individually.

The expected action for a given combination of two herbicides can be calculated as follows (cf. COLBY, S. R.: "Calculating synergistic and antagonistic responses of herbicide combinations", Weeds 15, pages 20–22, 1967):

If
X=% damage by herbicide A (active compound of the formula I) at an application rate of p kg/ha
and
Y=% damage by herbicide B (active compound of the formula II) at an application rate of q kg/ha
and
E=the expected damage of herbicides A+B at an application rate of p+q kg/ha,
then $$E = X + Y - (X*Y/100).$$

If the actual damage exceeds the calculated value, the combination has a superadditive effect, that is to say a synergistic effect.

The actual herbicidal activity of the active compound combinations of the present invention is higher than the calculated activity, i.e. the novel active compound combinations act synergistically.

This is apparent in particular from the examples below.

USE EXAMPLES

Customary formulations of the active compounds tested were used. Procarbazone- and flucarbazone-sodium were used as 70 WG formulation. Fenoxaprop-P-ethyl was used in a mixture with mefenpyr-diethyl (75 g of mefenpyr-diethyl/l) as Ralon® Super 69 EW. Cinidon-ethyl and florasulam and iodosufuron in a mixture with mefenpyr-diethyl were used in the form of the finished formulations Lotus® 200 EC, Primus® 50 SC and Hussar® 5 WG (15% mefenpyr-diethyl), respectively. Amicarbazone was used as 70 WG formulation.

The required amount of active compound or formulation is dissolved in a few millilitres(2–3 ml) of the solvent (acetone or DMF), optionally admixed with an emulsifier (1 ml) and diluted with water to the desired concentration.

Mixtures are prepared by mixing a predetermined dissolved amount of the first active compound with the required amount of the second active compound (and, if desired, with additional active compounds/formulations or other ingredients), followed by dilution with water to the desired concentration.

In pre- and post-emergence experiments, the spray liquor is usually admixed with a surfactant (Renex 36), at a concentration of 0.1%.

The amount of active compound or formulation is chosen such that the desired application rate per ha is achieved.

Example B

Post-Emergence/Greenhouse

Test plants are grown under controlled conditions (temperature and light). Once the plants have reached a height of 5 to 15 cm, the test compound or the combination of test compounds is applied by spraying such that the particular amounts of active compound desired are applied per unit area. The concentration of the spray liquor is chosen so that the particular amounts of active compound desired are applied in 500 l of water/ha.

Following the spray application, the plant containers are kept in a greenhouse under constant light and temperature conditions.

After about 3 weeks, the degree of damage to the plants is rated in % damage in comparison to the development of the untreated control.

The figures denote:

0%=no damage (like untreated control)
100%=total destruction/damage

Active compounds, application rates, test plants and results are shown in the tables below, the abbreviations used in the tables having the following meanings:

a.i.=active ingredient=active compound

TABLE B-1

|  | Application rate g of ai/ha | Alopecurus myosuroides observed | Alopecurus myosuroides calculated* |
|---|---|---|---|
| Procarbazone-sodium | 60 | 70 | |
|  | 30 | 70 | |
|  | 15 | 60 | |
| Fenoxaprop-P-ethyl | 30 | 0 | |
|  | 15 | 0 | |
| Procarbazone-sodium + fenoxaprop-P-ethyl | 60 + 30 | 80 | 70 |
|  | 30 + 30 | 80 | 70 |
|  | 15 + 30 | 80 | 60 |
|  | 30 + 15 | 80 | 70 |
|  | 15 + 15 | 80 | 60 |

Fenoxaprop-P-ethyl tested as Ralon ® super (fenoxaprop-P-ethyl 6.9% & mefenpyr 7.5%)
*Values calculated according to Colby

TABLE B-2

|  | Application rate g of ai/ha | Bromus secalinus observed | Bromus secalinus calculated* |
|---|---|---|---|
| Procarbazone-sodium | 15 | 80 | |
| Fenoxaprop-P-ethyl | 60 | 0 | |
|  | 30 | 0 | |
| Procarbazone-sodium + fenoxaprop-P-ethyl | 15 + 60 | 90 | 80 |
|  | 15 + 30 | 90 | 80 |

Fenoxaprop-P-ethyl tested as Ralon ® super (fenoxaprop-P-ethyl 6.9% & mefenpyr 7.5%)
*Values calculated according to Colby

TABLE B-3

|  | Application rate g of ai/ha | Lolium perenne observed | Lolium perenne calculated* |
|---|---|---|---|
| Procarbazone-sodium | 30 | 30 | |
|  | 15 | 0 | |
| Fenoxaprop-P-ethyl | 60 | 0 | |
|  | 30 | 0 | |
| Procarbazone-sodium + fenoxaprop-P-ethyl | 30 + 60 | 70 | 30 |
|  | 15 + 60 | 70 | 0 |
|  | 30 + 30 | 70 | 30 |
|  | 15 + 30 | 50 | 0 |

Fenoxaprop-P-ethyl tested as Ralon ® super (fenoxaprop-P-ethyl 6.9% & mefenpyr 7.5%)
*Values calculated according to Colby

TABLE B-4

|  | Application rate g of ai/ha | Amaranthus retroflexus observed | Amaranthus retroflexus calculated* |
|---|---|---|---|
| Procarbazone-sodium | 30 | 90 | |
|  | 15 | 80 | |
| Fenoxaprop-P-ethyl | 60 | 0 | |
|  | 30 | 0 | |
| Procarbazone-sodium + fenoxaprop-P-ethyl | 30 + 60 | 95 | 90 |
|  | 15 + 60 | 95 | 80 |
|  | 15 + 30 | 90 | 80 |

Fenoxaprop-P-ethyl tested as Ralon ® super (fenoxaprop-P-ethyl 6.9% & mefenpyr 7.5%)
*Values calculated according to Colby

TABLE B-5

|  | Application rate g of ai/ha | Galium aparine observed | Galium aparine calculated* |
|---|---|---|---|
| Procarbazone-sodium | 60 | 40 | |
|  | 30 | 30 | |
|  | 15 | 20 | |
| Fenoxaprop-P-ethyl | 60 | 0 | |
|  | 30 | 0 | |
|  | 15 | 0 | |
| Procarbazone-sodium + fenoxaprop-P-ethyl | 60 + 60 | 80 | 40 |
|  | 30 + 60 | 60 | 30 |
|  | 15 + 60 | 60 | 20 |
|  | 60 + 30 | 80 | 40 |
|  | 30 + 30 | 60 | 30 |
|  | 15 + 30 | 50 | 20 |
|  | 30 + 15 | 60 | 30 |
|  | 15 + 15 | 50 | 20 |

Fenoxaprop-P-ethyl tested as Ralon ® super (fenoxaprop-P-ethyl 6.9% & mefenpyr 7.5%)
*Values calculated according to Colby

TABLE B-6

|  | Application rate g of ai/ha | Ipomoea hederacea observed | Ipomoea hederacea calculated* |
|---|---|---|---|
| Procarbazone-sodium | 60 | 70 | |
|  | 30 | 70 | |
|  | 15 | 60 | |
| Fenoxaprop-P-ethyl | 60 | 0 | |
|  | 30 | 0 | |
| Procarbazone-sodium + fenoxaprop-P-ethyl | 60 + 60 | 80 | 70 |
|  | 30 + 60 | 80 | 70 |
|  | 15 + 60 | 80 | 60 |

TABLE B-6-continued

|  | Application rate g of ai/ha | Ipomoea hederacea observed | Ipomoea hederacea calculated* |
|---|---|---|---|
| ethyl | 60 + 30 | 80 | 70 |
|  | 15 + 30 | 80 | 60 |

Fenoxaprop-P-ethyl tested as Ralon ® super (fenoxaprop-P-ethyl 6.9% & mefenpyr 7.5%)
*Values calculated according to Colby

TABLE B-7

|  | Application rate g of ai/ha | Solanum nigrum observed | Solanum nigrum calculated* |
|---|---|---|---|
| Procarbazone-sodium | 30 | 70 | |
| Fenoxaprop-P-ethyl | 60 | 0 | |
|  | 30 | 0 | |
|  | 15 | 0 | |
| Procarbazone-sodium + fenoxaprop-P-ethyl | 30 + 60 | 100 | 70 |
|  | 30 + 30 | 90 | 70 |
|  | 30 + 15 | 90 | 70 |

Fenoxaprop-P-ethyl tested as Ralon ® super (fenoxaprop-P-ethyl 6.9% & mefenpyr 7.5%)
*Values calculated according to Colby

TABLE B-8

|  | Application rate g of ai/ha | Viola arvensis observed | Viola arvensis calculated* |
|---|---|---|---|
| Procarbazone-sodium | 30 | 50 | |
|  | 15 | 10 | |
| Fenoxaprop-P-ethyl | 60 | 0 | |
|  | 30 | 0 | |
|  | 15 | 0 | |
| Fenoxaprop-P-ethyl | 30 + 60 | 70 | 50 |
|  | 15 + 60 | 70 | 10 |
|  | 30 + 30 | 70 | 50 |
|  | 15 + 30 | 30 | 10 |
|  | 15 + 15 | 30 | 10 |

Fenoxaprop-P-ethyl tested as Ralon ® super (fenoxaprop-P-ethyl 6.9% & mefenpyr 7.5%)
*Values calculated according to Colby

TABLE B-9

|  | Application rate g of ai/ha | Xanthium strumarium observed | Xanthium strumarium calculated* |
|---|---|---|---|
| Procarbazone-sodium | 30 | 70 | |
|  | 15 | 60 | |
| Fenoxaprop-P-ethyl | 60 | 0 | |
|  | 30 | 0 | |
| Procarbazone-sodium + fenoxaprop-P-ethyl | 30 + 60 | 90 | 70 |
|  | 15 + 60 | 80 | 60 |
|  | 30 + 30 | 80 | 70 |

Fenoxaprop-P-ethyl tested as Ralon ® super (fenoxaprop-P-ethyl 6.9% & mefenpyr 7.5%)
*Values calculated according to Colby

TABLE B-10

| | Application rate g of ai/ha | Bromus secalinus observed | Bromus secalinus calculated* |
|---|---|---|---|
| Flucarbazone-sodium | 60 | 80 | |
| | 30 | 70 | |
| | 15 | 70 | |
| Fenoxaprop-P-ethyl | 60 | 0 | |
| | 30 | 0 | |
| Flucarbazone-sodium + fenoxaprop-P-ethyl | 15 + 60 | 90 | 70 |
| | 60 + 30 | 90 | 80 |
| | 30 + 30 | 90 | 70 |
| | 15 + 30 | 90 | 70 |

Fenoxaprop-P-ethyl tested as Ralon ® super (fenoxaprop-P-ethyl 6.9% & mefenpyr 7.5%)
*Values calculated according to Colby

TABLE B-11

| | Application rate g of ai/ha | Amaranthus retroflexus observed | Amaranthus retroflexus calculated* |
|---|---|---|---|
| Flucarbazone-sodium | 30 | 90 | |
| | 15 | 90 | |
| Fenoxaprop-P-ethyl | 60 | 0 | |
| | 30 | 0 | |
| Flucarbazone-sodium + fenoxaprop-P-ethyl | 15 + 60 | 100 | 90 |
| | 30 + 30 | 100 | 90 |
| | 15 + 30 | 100 | 90 |

Fenoxaprop-P-ethyl tested as Ralon ® super (fenoxaprop-P-ethyl 6.9% & mefenpyr 7.5%)
*Values calculated according to Colby

TABLE B-12

| | Application rate g of ai/ha | Chenopodium album observed | Chenopodium album calculated* |
|---|---|---|---|
| Flucarbazone-sodium | 60 | 70 | |
| | 30 | 50 | |
| | 15 | 50 | |
| Fenoxaprop-P-ethyl | 60 | 0 | |
| | 30 | 0 | |
| Flucarbazone-sodium + fenoxaprop-P-ethyl | 60 + 60 | 90 | 70 |
| | 15 + 60 | 80 | 50 |
| | 30 + 30 | 70 | 50 |
| | 15 + 30 | 70 | 50 |

Fenoxaprop-P-ethyl tested as Ralon ® super (fenoxaprop-P-ethyl 6.9% & mefenpyr 7.5%)
*Values calculated according to Colby

TABLE B-13

| | Application rate g of ai/ha | Datura strumarium observed | Datura strumarium calculated* |
|---|---|---|---|
| Flucarbazone-sodium | 60 | 80 | |
| | 15 | 70 | |
| Fenoxaprop-P-ethyl | 60 | 0 | |
| | 30 | 0 | |
| Flucarbazone-sodium + fenoxaprop-P-ethyl | 60 + 60 | 98 | 80 |
| | 15 + 30 | 90 | 70 |

Fenoxaprop-P-ethyl tested as Ralon ® super (fenoxaprop-P-ethyl 6.9% & mefenpyr 7.5%)
*Values calculated according to Colby

TABLE B-14

| | Application rate g of ai/ha | Galium aparine observed | Galium aparine calculated* |
|---|---|---|---|
| Flucarbazone-sodium | 60 | 0 | |
| | 30 | 0 | |
| | 15 | 0 | |
| Fenoxaprop-P-ethyl | 60 | 0 | |
| | 30 | 0 | |
| Flucarbazone-sodium + fenoxaprop-P-ethyl | 60 + 60 | 60 | 0 |
| | 30 + 60 | 50 | 0 |
| | 15 + 60 | 50 | 0 |
| | 60 + 30 | 50 | 0 |
| | 30 + 30 | 50 | 0 |
| | 15 + 30 | 50 | 0 |

Fenoxaprop-P-ethyl tested as Ralon ® super (fenoxaprop-P-ethyl 6.9% & mefenpyr 7.5%)
*Values calculated according to Colby

TABLE B-15

| | Application rate g of ai/ha | Polygonum convolvolus observed | Polygonum convolvolus calculated* |
|---|---|---|---|
| Flucarbazone-sodium | 60 | 70 | |
| | 30 | 70 | |
| | 15 | 60 | |
| Fenoxaprop-P-ethyl | 60 | 0 | |
| | 30 | 0 | |
| Flucarbazone-sodium + fenoxaprop-P-ethyl | 60 + 60 | 95 | 70 |
| | 15 + 60 | 90 | 60 |
| | 60 + 30 | 90 | 70 |
| | 30 + 30 | 90 | 70 |
| | 15 + 30 | 90 | 60 |

Fenoxaprop-P-ethyl tested as Ralon ® super (fenoxaprop-P-ethyl 6.9% & mefenpyr 7.5%)
*Values calculated according to Colby

TABLE B-16

| | Application rate g off ai/ha | Stellaria media observed | Stellaria media calculated* |
|---|---|---|---|
| Flucarbazone-sodium | 60 | 95 | |
| | 30 | 60 | |
| | 15 | 0 | |
| Fenoxaprop-P-ethyl | 60 | 0 | |
| | 30 | 0 | |
| Flucarbazone-sodium + fenoxaprop-P-ethyl | 60 + 60 | 100 | 95 |
| | 15 + 60 | 100 | 0 |
| | 30 + 30 | 90 | 60 |
| | 15 + 30 | 50 | 0 |

Fenoxaprop-P-ethyl tested as Ralon ® super (fenoxaprop-P-ethyl 6.9% & mefenpyr 7.5%)
*Values calculated according to Colby

TABLE B-17

| | Application rate g of ai/ha | Viola arvensis observed | Viola arvensis calculated* |
|---|---|---|---|
| Flucarbazone-sodium | 15 | 60 | |
| Fenoxaprop-P-ethyl | 60 | 0 | |
| | 30 | 0 | |
| Flucarbazone-sodium + fenoxaprop-P-ethyl | 15 + 60 | 90 | 60 |
| | 15 + 30 | 80 | 60 |

Fenoxaprop-P-ethyl tested as Ralon ® super (fenoxaprop-P-ethyl 6.9% & mefenpyr 7.5%)
*Values calculated according to Colby

TABLE B-18

|  | Application rate g of ai/ha | Avena fatua observed | Avena fatua calculated* |
|---|---|---|---|
| Procarbazone-sodium | 30 | 90 | |
|  | 15 | 70 | |
| Flufenacet | 125 | 70 | |
| Procarbazone-sodium + flufenacet | 30 + 125 | 100 | 97 |
|  | 15 + 125 | 100 | 91 |

*Values calculated according to Colby

TABLE B-19

|  | Application rate g of ai/ha | Amaranthus retroflexus observed | Amaranthus retroflexus calculated* |
|---|---|---|---|
| Procarbazone-sodium | 60 | 98 | |
|  | 30 | 98 | |
|  | 15 | 98 | |
| Flufenacet | 125 | 0 | |
|  | 60 | 0 | |
| Procarbazone-sodium + flufenacet | 60 + 125 | 100 | 98 |
|  | 30 + 125 | 100 | 98 |
|  | 60 + 60 | 100 | 98 |
|  | 30 + 60 | 100 | 98 |
|  | 15 + 60 | 100 | 98 |

*Values calculated according to Colby

TABLE B-20

|  | Application rate g of ai/ha | Polygonum convolvolus observed | Polygonum convolvolus calculated* |
|---|---|---|---|
| Procarbazone-sodium | 60 | 0 | |
| Flufenacet | 125 | 0 | |
| Procarbazone-sodium + flufenacet | 60 + 125 | 40 | 0 |

*Values calculated according to Colby

TABLE B-21

|  | Application rate g of ai/ha | Alopecurus myosuroides observed | Alopecurus myosuroides calculated* |
|---|---|---|---|
| Procarbazone-sodium | 60 | 90 | |
|  | 30 | 80 | |
|  | 15 | 80 | |
| Cinidon-ethyl | 15 | 0 | |
|  | 8 | 0 | |
| Procarbazone-sodium + cinidon-ethyl | 60 + 15 | 95 | 90 |
|  | 30 + 15 | 99 | 80 |
|  | 60 + 8 | 95 | 90 |
|  | 30 + 8 | 95 | 80 |
|  | 15 + 8 | 90 | 80 |

*Values calculated according to Colby

TABLE B-22

|  | Application rate g of ai/ha | Avena fatua observed | Avena fatua calculated* |
|---|---|---|---|
| Procarbazone-sodium | 60 | 60 | |
|  | 30 | 50 | |
|  | 15 | 50 | |

TABLE B-22-continued

|  | Application rate g of ai/ha | Avena fatua observed | Avena fatua calculated* |
|---|---|---|---|
| Cinidon-ethyl | 15 | 10 | |
|  | 8 | 0 | |
| Procarbazone-sodium + cinidon-ethyl | 60 + 15 | 90 | 64 |
|  | 30 + 15 | 70 | 55 |
|  | 15 + 15 | 80 | 55 |
|  | 60 + 8 | 70 | 60 |
|  | 30 + 8 | 90 | 50 |
|  | 15 + 8 | 80 | 50 |

*Values calculated according to Colby

TABLE B-23

|  | Application rate g of ai/ha | Bromus secalinus observed | Bromus secalinus calculated* |
|---|---|---|---|
| Procarbazone-sodium | 60 | 90 | |
|  | 30 | 80 | |
|  | 15 | 70 | |
| Cinidon-ethyl | 15 | 20 | |
|  | 8 | 0 | |
| Procarbazone-sodium + cinidon-ethyl | 60 + 15 | 99 | 92 |
|  | 30 + 15 | 90 | 84 |
|  | 15 + 15 | 80 | 76 |
|  | 60 + 8 | 95 | 90 |
|  | 30 + 8 | 95 | 80 |
|  | 15 + 8 | 80 | 70 |

*Values calculated according to Colby

TABLE B-24

|  | Application rate g of ai/ha | Cyperus esculentus observed | Cyperus esculentus calculated* |
|---|---|---|---|
| Procarbazone-sodium | 30 | 80 | |
|  | 15 | 70 | |
| Cinidon-ethyl | 15 | 20 | |
|  | 8 | 0 | |
| Procarbazone-sodium + cinidon-ethyl | 30 + 15 | 95 | 84 |
|  | 30 + 8 | 90 | 80 |
|  | 15 + 8 | 95 | 70 |

*Values calculated according to Colby

TABLE B-25

|  | Application rate g of ai/ha | Echinochloa crus-galli observed | Echinochloa crus-galli calculated* |
|---|---|---|---|
| Procarbazone-sodium | 60 | 90 | |
|  | 30 | 90 | |
| Cinidon-ethyl | 15 | 0 | |
|  | 8 | 0 | |
| Procarbazone-sodium + cinidon-ethyl | 60 + 15 | 99 | 90 |
|  | 30 + 8 | 100 | 90 |

*Values calculated according to Colby

TABLE B-26

|  | Application rate g of ai/ha | Eriochloa villosa observed | Eriochloa villosa calculated* |
|---|---|---|---|
| Procarbazone-sodium | 15 | 0 | |

TABLE B-26-continued

| | Application rate g of ai/ha | Eriochloa villosa observed | Eriochloa villosa calculated* |
|---|---|---|---|
| Cinidon-ethyl | 15 | 30 | |
| Procarbazone-sodium + cinidon-ethyl | 15 + 15 | 80 | 30 |

*Values calculated according to Colby

TABLE B-27

| | Application rate g of ai/ha | Lolium perenne observed | Lolium perenne calculated* |
|---|---|---|---|
| Procarbazone-sodium | 30 | 20 | |
| Cinidon-ethyl | 8 | 0 | |
| Procarbazone-sodium + cinidon-ethyl | 30 + 8 | 70 | 20 |

*Values calculated according to Colby

TABLE B-28

| | Application rate g of ai/ha | Cassia tora observed | Cassia tora calculated* |
|---|---|---|---|
| Procarbazone-sodium | 30 | 0 | |
| Cinidon-ethyl | 15 | 95 | |
| Procarbazone-sodium + cinidon-ethyl | 30 + 15 | 100 | 95 |

*Values calculated according to Colby

TABLE B-29

| | Application rate g of ai/ha | Viola arvensis observed | Viola arvensis calculated* |
|---|---|---|---|
| Procarbazone-sodium | 60 | 80 | |
| | 30 | 70 | |
| | 15 | 50 | |
| Cinidon-ethyl | 15 | 30 | |
| | 8 | 0 | |
| Procarbazone-sodium + cinidon-ethyl | 60 + 15 | 95 | 86 |
| | 30 + 15 | 90 | 79 |
| | 15 + 15 | 90 | 65 |
| | 60 + 8 | 90 | 80 |
| | 30 + 8 | 80 | 70 |
| | 15 + 8 | 60 | 50 |

*Values calculated according to Colby

TABLE B-30

| | Application rate g of ai/ha | Avena fatua observed | Avena fatua calculated* |
|---|---|---|---|
| Procarbazone-sodium | 60 | 60 | |
| | 30 | 50 | |
| Florasulam | 15 | 50 | |
| | 8 | 30 | |
| Procarbazone-sodium + florasulam | 60 + 15 | 90 | 80 |
| | 30 + 8 | 80 | 65 |

*Values calculated according to Colby

TABLE B-31

| | Application rate g of ai/ha | Lolium perenne observed | Lolium perenne calculated* |
|---|---|---|---|
| Procarbazone-sodium | 60 | 50 | |
| | 30 | 20 | |
| Florasulam | 15 | 30 | |
| | 8 | 20 | |
| Procarbazone-sodium + florasulam | 60 + 15 | 70 | 65 |
| | 30 + 15 | 70 | 44 |
| | 30 + 8 | 60 | 36 |

*Values calculated according to Colby

TABLE B-32

| | Application rate g of ai/ha | Cassia tora observed | Cassia tora calculated* |
|---|---|---|---|
| Procarbazone-sodium | 60 | 30 | |
| | 30 | 0 | |
| Florasulam | 15 | 95 | |
| | 8 | 90 | |
| Procarbazone-sodium + florasulam | 60 + 15 | 100 | 96.5 |
| | 30 + 8 | 95 | 90 |

*Values calculated according to Colby

TABLE B-33

| | Application rate g of ai/ha | Polygonum convolvolus observed | Polygonum convolvolus calculated* |
|---|---|---|---|
| Procarbazone-sodium | 60 | 0 | |
| | 30 | 0 | |
| Florasulam | 15 | 95 | |
| | 8 | 95 | |
| Procarbazone-sodium + florasulam | 30 + 15 | 99 | 95 |
| | 60 + 8 | 99 | 95 |
| | 30 + 8 | 99 | 95 |

*Values calculated according to Colby

TABLE B-34

| | Application rate g of ai/ha | Viola arvensis observed | Viola arvensis calculated* |
|---|---|---|---|
| Procarbazone-sodium | 15 | 50 | |
| Florasulam | 8 | 70 | |
| Procarbazone-sodium + florasulam | 15 + 8 | 90 | 85 |

*Values calculated according to Colby

TABLE B-35

| | Application rate g of ai/ha | Alopecurus myosuroides observed | Alopecurus myosuroides calculated* |
|---|---|---|---|
| Flucarbazone-sodium | 60 | 70 | |
| | 30 | 70 | |
| | 15 | 70 | |
| Florasulam | 4 | 0 | |
| | 2 | 0 | |
| Flucarbazone-sodium + florasulam | 15 + 4 | 90 | 70 |
| | 60 + 2 | 95 | 70 |
| | 30 + 2 | 90 | 70 |

*Values calculated according to Colby

TABLE B-36

|  | Application rate g of ai/ha | Avena fatua observed | Avena fatua calculated* |
|---|---|---|---|
| Flucarbazone-sodium | 60 | 90 |  |
|  | 30 | 90 |  |
|  | 15 | 80 |  |
| Florasulam | 4 | 10 |  |
|  | 2 | 0 |  |
| Flucarbazone-sodium + florasulam | 60 + 4 | 95 | 91 |
|  | 30 + 4 | 95 | 91 |
|  | 15 + 4 | 95 | 82 |
|  | 60 + 2 | 98 | 90 |
|  | 30 + 2 | 98 | 90 |
|  | 15 + 2 | 90 | 80 |

*Values calculated according to Colby

TABLE B-37

|  | Application rate g of ai/ha | Bromus secalinus observed | Bromus secalinus calculated* |
|---|---|---|---|
| Flucarbazone-sodium | 60 | 90 |  |
|  | 30 | 90 |  |
|  | 15 | 70 |  |
| Florasulam | 4 | 0 |  |
|  | 2 | 0 |  |
| Flucarbazone-sodium + florasulam | 60 + 4 | 98 | 90 |
|  | 30 + 4 | 100 | 90 |
|  | 15 + 4 | 90 | 70 |
|  | 60 + 2 | 100 | 90 |
|  | 15 + 2 | 80 | 70 |

*Values calculated according to Colby

TABLE B-38

|  | Application rate g of ai/ha | Digitaria sanguinalis observed | Digitaria sanguinalis calculated* |
|---|---|---|---|
| Flucarbazone-sodium | 60 | 20 |  |
|  | 30 | 20 |  |
| Florasulam | 4 | 0 |  |
|  | 2 | 0 |  |
| Flucarbazone-sodium + florasulam | 60 + 4 | 60 | 20 |
|  | 30 + 4 | 60 | 20 |
|  | 60 + 2 | 80 | 20 |

*Values calculated according to Colby

TABLE B-39

|  | Application rate g of ai/ha | Echinochloa crus-galli observed | Echinochloa crus-galli calculated* |
|---|---|---|---|
| Flucarbazone-sodium | 60 | 90 |  |
|  | 15 | 50 |  |
| Florasulam | 4 | 40 |  |
|  | 2 | 10 |  |
| Flucarbazone-sodium + florasulam | 60 + 4 | 98 | 94 |
|  | 15 + 4 | 80 | 70 |
|  | 60 + 2 | 100 | 91 |
|  | 15 + 2 | 70 | 55 |

*Values calculated according to Colby

TABLE B-40

|  | Application rate g of ai/ha | Lolium perenne observed | Lolium perenne calculated* |
|---|---|---|---|
| Flucarbazone-sodium | 60 | 90 |  |
|  | 30 | 90 |  |
|  | 15 | 80 |  |
| Florasulam | 4 | 0 |  |
|  | 2 | 0 |  |
| Flucarbazone-sodium + florasulam | 60 + 4 | 95 | 90 |
|  | 30 + 4 | 95 | 90 |
|  | 15 + 4 | 90 | 80 |
|  | 60 + 2 | 100 | 90 |
|  | 30 + 2 | 98 | 90 |

*Values calculated according to Colby

TABLE B-41

|  | Application rate g of ai/ha | Abutilon theophrasti observed | Abutilon theophrasti calculated* |
|---|---|---|---|
| Flucarbazone-sodium | 60 | 0 |  |
|  | 30 | 0 |  |
|  | 15 | 0 |  |
| Florasulam | 4 | 30 |  |
|  | 2 | 20 |  |
| Flucarbazone-sodium + florasulam | 60 + 4 | 60 | 30 |
|  | 30 + 4 | 60 | 30 |
|  | 15 + 4 | 60 | 30 |
|  | 60 + 2 | 70 | 20 |
|  | 30 + 2 | 70 | 20 |

*Values calculated according to Colby

TABLE B-42

|  | Application rate g of ai/ha | Amaranthus retroflexus observed | Amaranthus retroflexus calculated* |
|---|---|---|---|
| Flucarbazone-sodium | 60 | 90 |  |
|  | 30 | 90 |  |
|  | 15 | 90 |  |
| Florasulam | 4 | 70 |  |
|  | 2 | 70 |  |
| Flucarbazone-sodium + florasulam | 60 + 4 | 100 | 97 |
|  | 30 + 4 | 100 | 97 |
|  | 15 + 4 | 100 | 97 |
|  | 60 + 2 | 100 | 97 |
|  | 30 + 2 | 100 | 97 |

*Values calculated according to Colby

TABLE B-43

|  | Application rate g of ai/ha | Galium aparine observed | Galium aparine calculated* |
|---|---|---|---|
| Flucarbazone-sodium | 60 | 0 |  |
|  | 30 | 0 |  |
|  | 15 | 0 |  |
| Florasulam | 4 | 50 |  |
|  | 2 | 50 |  |
| Flucarbazone-sodium + florasulam | 60 + 4 | 70 | 50 |
|  | 30 + 4 | 70 | 50 |
|  | 15 + 4 | 60 | 50 |
|  | 60 + 2 | 90 | 50 |

*Values calculated according to Colby

TABLE B-44

|  | Application rate g of ai/ha | Matricaria inodora observed | Matricaria inodora calculated* |
|---|---|---|---|
| Flucarbazone-sodium | 60 | 20 | |
| Florasulam | 2 | 70 | |
| Flucarbazone-sodium + florasulam | 60 + 2 | 98 | 76 |

*Values calculated according to Colby

TABLE B-45

|  | Application rate g of ai/ha | Veronica persicaria observed | Veronica persicaria calculated* |
|---|---|---|---|
| Flucarbazone-sodium | 60 | 0 | |
| Florasulam | 4 | 0 | |
|  | 2 | 0 | |
| Flucarbazone-sodium + florasulam | 60 + 4 | 40 | 0 |
|  | 60 + 2 | 70 | 0 |

*Values calculated according to Colby

TABLE B-46

|  | Application rate g of ai/ha | Viola arvensis observed | Viola arvensis calculated* |
|---|---|---|---|
| Flucarbazone-sodium | 60 | 50 | |
|  | 30 | 50 | |
|  | 15 | 50 | |
| Florasulam | 4 | 0 | |
|  | 2 | 0 | |
| Flucarbazone-sodium + florasulam | 60 + 4 | 100 | 50 |
|  | 30 + 4 | 80 | 50 |
|  | 15 + 4 | 80 | 50 |
|  | 60 + 2 | 98 | 50 |
|  | 30 + 2 | 90 | 50 |

*Values calculated according to Colby

TABLE B-47

|  | Application rate g of ai/ha | Xanthium strumarium observed | Xanthium strumarium calculated* |
|---|---|---|---|
| Flucarbazone-sodium | 60 | 60 | |
|  | 30 | 40 | |
|  | 15 | 20 | |
| Florasulam | 4 | 50 | |
|  | 2 | 40 | |
| Flucarbazone-sodium + florasulam | 30 + 4 | 80 | 70 |
|  | 15 + 4 | 70 | 60 |
|  | 60 + 2 | 80 | 76 |
|  | 30 + 2 | 70 | 64 |
|  | 15 + 2 | 70 | 52 |

*Values calculated according to Colby

TABLE B-48

|  | Application rate g of ai/ha | Cassia tora observed | Cassia tora calculated* |
|---|---|---|---|
| Procarbazone-sodium | 60 | 50 | |
|  | 30 | 50 | |
|  | 15 | 50 | |
| Amicarbazone | 30 | 40 | |
| Procarbazone-sodium + amicarbazone | 60 + 30 | 100 | 70 |
|  | 30 + 30 | 98 | 70 |
|  | 15 + 30 | 98 | 70 |

*Values calculated according to Colby

TABLE B-49

|  | Application rate g of ai/ha | Stellaria media observed | Stellaria media calculated* |
|---|---|---|---|
| Procarbazone-sodium | 60 | 70 | |
|  | 30 | 60 | |
|  | 15 | 50 | |
| Amicarbazone | 60 | 80 | |
| Procarbazone-sodium + amicarbazone | 60 + 60 | 100 | 94 |
|  | 30 + 60 | 100 | 92 |
|  | 15 + 60 | 100 | 90 |

*Values calculated according to Colby

TABLE B-50

|  | Application rate g of ai/ha | Viola arvensis observed | Viola arvensis calculated* |
|---|---|---|---|
| Procarbazone-sodium | 15 | 60 | |
| Amicarbazone | 30 | 70 | |
| Procarbazone-sodium + amicarbazone | 15 + 30 | 100 | 88 |

*Values calculated according to Colby

TABLE B-51

|  | Application rate g of ai/ha | Xanthium strumarium observed | Xanthium strumarium calculated* |
|---|---|---|---|
| Procarbazone-sodium | 60 | 60 | |
|  | 30 | 60 | |
| Amicarbazone | 30 | 80 | |
| Procarbazone-sodium + amicarbazone | 60 + 30 | 98 | 92 |
|  | 30 + 30 | 98 | 92 |

*Values calculated according to Colby

TABLE B-52

|  | Application rate g of ai/ha | Abutilon theophrasti observed | Abutilon theophrasti calculated* |
|---|---|---|---|
| Procarbazone-sodium | 60 | 60 | |
| Amicarbazone | 30 | 80 | |
| Procarbazone-sodium + amicarbazone | 60 + 30 | 98 | 92 |

*Values calculated according to Colby

TABLE B-53

| | Application rate g of ai/ha | *Eriochloa villosa* observed | *Eriochloa villosa* calculated* |
|---|---|---|---|
| Flucarbazone-sodium | 60 | 70 | |
| Amicarbazone | 125 | 70 | |
| Flucarbazone-sodium + amicarbazone | 60 + 125 | 100 | 91 |

*Values calculated according to Colby

TABLE B-54

| | Application rate g of ai/ha | *Viola arvensis* observed | *Viola arvensis* calculated* |
|---|---|---|---|
| Flucarbazone-sodium | 15 | 80 | |
| Amicarbazone | 30 | 70 | |
| Flucarbazone-sodium + amicarbazone | 15 + 30 | 100 | 94 |

*Values calculated according to Colby

TABLE B-55

| | Application rate G of ai/ha | *Cassia tora* observed | *Cassia tora* calculated* |
|---|---|---|---|
| Flucarbazone-sodium | 60 | 50 | |
| | 30 | 50 | |
| | 15 | 50 | |
| Amicarbazone | 30 | 40 | |
| Flucarbazone-sodium + amicarbazone | 60 + 30 | 100 | 70 |
| | 30 + 30 | 100 | 70 |
| | 15 + 30 | 100 | 70 |

*Values calculated according to Colby

TABLE B-56

| | Application rate g off ai/ha | *Matricaria inodora* observed | *Matricaria inodora* calculated* |
|---|---|---|---|
| Flucarbazone-sodium | 60 | 60 | |
| | 30 | 60 | |
| | 15 | 20 | |
| Amicarbazone | 30 | 60 | |
| Flucarbazone-sodium + amicarbazone | 60 + 30 | 98 | 84 |
| | 30 + 30 | 90 | 84 |
| | 15 + 30 | 90 | 68 |

*Values calculated according to Colby

TABLE B-57

| | Application rate g of ai/ha | *Avena fatua* observed | *Avena fatua* calculated* |
|---|---|---|---|
| Flucarbazone-sodium | 60 | 70 | |
| | 30 | 70 | |
| | 15 | 70 | |
| Amicarbazone | 30 | 0 | |
| flucarbazone-sodium + amicarbazone | 60 + 30 | 98 | 70 |
| | 30 + 30 | 95 | 70 |
| | 15 + 30 | 80 | 70 |

*Values calculated according to Colby

TABLE B-58

| | Application rate g of ai/ha | *Avena fatua* observed | *Avena fatua* calculated* |
|---|---|---|---|
| Procarbazone-sodium | 15 | 80 | |
| Iodosulfuron | 8 | 70 | |
| Procarbazone-sodium + iodosulfuron | 15 + 8 | 98 | 94 |

Iodosulfuron tested as Hussar ® (iodosulfuron 5% & mefenpyr 15%)
*Values calculated according to Colby

TABLE B-59

| | Application rate g of ai/ha | *Bromus secalinus* observed | *Bromus secalinus* calculated* |
|---|---|---|---|
| Procarbazone-sodium | 30 | 90 | |
| | 15 | 90 | |
| Iodosulfuron | 8 | 0 | |
| | 4 | 0 | |
| | 2 | 0 | |
| Procarbazone-sodium + iodosulfuron | 30 + 8 | 95 | 90 |
| | 30 + 4 | 95 | 90 |
| | 15 + 4 | 95 | 90 |
| | 30 + 2 | 95 | 90 |

Iodosulfuron tested as Hussar ® (iodosulfuron 5% & mefenpyr 15%)
*Values calculated according to Colby

TABLE B-60

| | Application rate g of ai/ha | *Setaria viridis* observed | *Setaria viridis* calculated* |
|---|---|---|---|
| Procarbazone-sodium | 60 | 20 | |
| | 30 | 0 | |
| | 15 | 0 | |
| Iodosulfuron | 4 | 0 | |
| Procarbazone-sodium + iodosulfuron | 60 + 4 | 60 | 20 |
| | 30 + 4 | 40 | 0 |
| | 15 + 4 | 30 | 0 |

Iodosulfuron tested as Hussar ® (iodosulfuron 5% & mefenpyr 15%)
*Values calculated according to Colby

TABLE B-61

| | Application rate g of ai/ha | *Polygonum convolvolus* observed | *Polygonum convolvolus* calculated* |
|---|---|---|---|
| Procarbazone-sodium | 60 | 0 | |
| | 30 | 0 | |
| | 15 | 0 | |
| Iodosulfuron | 2 | 80 | |
| Procarbazone-sodium + iodosulfuron | 60 + 2 | 100 | 80 |
| | 30 + 2 | 95 | 80 |
| | 15 + 2 | 90 | 80 |

Iodosulfuron tested as Hussar ® (iodosulfuron 5% & mefenpyr 15%)
*Values calculated according to Colby

TABLE B-62

| | Application rate g of ai/ha | *Avena fatua* observed | *Avena fatua* calculated* |
|---|---|---|---|
| Flucarbazone-sodium | 15 | 80 | |
| Iodosulfuron | 2 | 10 | |

TABLE B-62-continued

| | Application rate g of ai/ha | Avena fatua observed | Avena fatua calculated* |
|---|---|---|---|
| Flucarbazone-sodium + iodosulfuron | 15 + 2 | 95 | 82 |

Iodosulfuron tested as Hussar ® (iodosulfuron 5% & mefenpyr 15%)
*Values calculated according to Colby

TABLE B-63

| | Application rate g of ai/ha | Echinochloa crus-galli observed | Echinochloa crus-galli calculated* |
|---|---|---|---|
| Flucarbazone-sodium | 60 | 90 | |
| | 30 | 70 | |
| | 15 | 60 | |
| Iodosulfuron | 2 | 20 | |
| Flucarbazone-sodium + iodosulfuron | 60 + 2 | 98 | 92 |
| | 30 + 2 | 95 | 76 |
| | 15 + 2 | 90 | 68 |

Iodosulfuron tested as Hussar ® (iodosulfuron 5% & mefenpyr 15%)
*Values calculated according to Colby

TABLE B-64

| | Application rate g of ai/ha | Cassia tora observed | Cassia tora calculated* |
|---|---|---|---|
| Flucarbazone-sodium | 15 | 0 | |
| Iodosulfuron | 8 | 80 | |
| Flucarbazone-sodium + iodosulfuron | 15 + 8 | 90 | 80 |

Iodosulfuron tested as Hussar ® (iodosulfuron 5% & mefenpyr 15%)
*Values calculated according to Colby

What is claimed is:

1. A composition comprising an active compound combination of:
(a) an arylsulphonylaminocarbonyltriazolinone selected from the group consisting of the compound 2-(2-methoxycarbonyl-phenysulphonylaminocarbonyl)-4-methyl-5-n-propoxy-2,4-dihydro-3H-1,2,4-triazol-3-one (procarbazone or propoxicarbazone), the compound 2-(2-trifluoromethoxy-phenysulphonylaminocarbonyl)-4-methyl-5-methoxy-2,4-dihydro-3H-1,2,4-triazol-3-one (flucarbazone) and a sodium salt of these two compounds (propoxicarbazone-sodium or flucarbazone-sodium) ("active compounds of group 1") and
(b) one to three compounds selected from a second group of herbicides comprising the active compounds listed below:
ethyl 2-chloro-3-[2-chloro-5-(1,3,4,5,6,7-hexahydro-1,3-dioxo-2H-isoindol-2-yl-phenyl]-2-propanoate (cinidon-ethyl), N-(2,6-difluoro-phenyl)-8-fluoro-5-methoxy-[1,2,4]-triazolo-[1,5-c]-pyrimidine-2-sulphonamide (florasulam), (R)-2-[4-(3-chloro-5-trifluoromethyl-pyridin-2-yl-oxy)-phenoxy]-propanoic acid (methyl ester, 2-ethoxy-ethyl ester, butyl ester) (haloxyfop, -methyl, -P-methyl, -ethoxyethyl, -butyl), N-(4-methoxy-6-methyl-1,3,5-triazin-2-yl)-N'-(5-iodo-2-methoxycarbonyl-phenylsulphonyl)-urea sodium salt (iodosulfuron-methyl-sodium), methyl 2-[[[[(4,6-dimethoxy-2-pyrimidinyl)-amino]-carbonyl]-amino]-sulphonyl]-4-[[(methylsulphonyl)-amino]methyl]-benzoate (mesosulfuron),
("active compounds of group 2"), and optionally
(c) a compound which improves crop plant compatibility selected from the group of compounds below:
4-dichloroacetyl-1-oxa-4-aza-spiro[4.5]-decane, 1-dichloroacetyl-hexahydro-3,3,8a-trimethylpyrrolo[1,2-a]-pyrimidin-6(2H)-one (dicyclonon), 4-dichloroacetyl-3,4-dihydro-3-methyl-2H-1,4-benzoxazine (benoxacor), 1-methyl-hexyl 5-chloro-quinolin-8-oxy-acetate (cloquintocet-mexyl), 3-(2-chloro-benzyl)-1-(1-methyl-1-phenyl-ethyl)-urea (cumyluron), α-(cyanomethoximino)-phenylacetonitrile (cyometrinil), 2,4-dichloro-phenoxy acetic acid (2,4-D), 1-(1-methyl-1-phenyl-ethyl)-3-(4-methyl-phenyl)-urea (daimuron, dymron), 3,6-dichloro-2-methoxy-benzoic acid (dicamba), S-1-methyl-1-phenyl-ethyl piperidine-1-thiocarboxylate (dimepiperate), 2,2-dichloro-N-(2-oxo-2-(2-propenylamino)-ethyl)-N-(2-propenyl)-acetamide, 2,2-dichloro-N,N-di-2-propenyl acetamide (dichlormid), 4,6-dichloro-2-phenyl-pyrimidine (fenclorim), ethyl 1-(2,4-dichloro-phenyl)-5-trichloro-methyl-1H-1,2,4-triazole-3-carboxylate (fenchlorazole-ethyl), phenylmethyl 2-chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole,), ethyl-4,5-dihydro-5,5-diphenyl-3-isoxazolecarboxylate (isoxadifen-ethyl), diethyl-1-(2,4-dichloro-phenyl)4,5-dihydro-5-methyl-1H-pyrazole-3,5-dicarboxylate (mefenpyr-diethyl), 2-dichloromethyl-2-methyl-1,3-dioxolane, 1,8-naphthalic anhydride, α-(1,3-dioxolan-2-yl-methoximino)-phenylacetonitrile (oxabetrinil), 2,2-dichloro-N-(1,3-dioxolan-2-yl-methyl)-N-(2-propenyl)-acetamide, 3-dichloroacetyl-2,2-dimethyl-oxazolidine, 3-dichloroacetyl-2,2,5-trimethyl-oxazolidine, methyl 1-(2-chloro-phenyl)-5-phenyl-1H-pyrazole-3-carboxylate, ethyl 1-(2,4-dichloro-phenyl)-5-methyl-1H-pyrazole-3-carboxylate, ethyl 1-(2,4-dichloro-phenyl)-5-isopropyl-1H-pyrazole-3-carboxylate, ethyl 1-(2,4-dichloro-phenyl)-5-(1,1-dimethyl-ethyl))-1H-pyrazole-3-carboxylate, ethyl 1-(2,4-dichloro-phenyl)-5-phenyl-1H-pyrazole-3-carboxylate, ethyl 5-(2,4-dichloro-benzyl)-2-isoxazoline-3-carboxylate, ethyl 5-phenyl-2-isoxazoline-3-carboxylate, ethyl 5-(4-fluoro-phenyl)-5-phenyl-2-isoxazoline-3-carboxylate, 1,3-dimethyl-but-1-yl 5-chloro-quinolin-8-oxy-acetate, 4-allyloxy-butyl 5-chloro-quinolin-8-oxy-acetate, 1-allyloxy-prop-2-yl 5-chloro-quinolin-8-oxy-acetate, methyl 5-chloro-quinolin-8-oxy-acetate, ethyl 5-chloro-quinolin-8-oxy-acetate, allyl 5-chloro-quinolin-8-oxy-acetate, 2-oxo-prop-1-yl 5-chloro-quinolin-8-oxy-acetate, diethyl 5-chloro-quinolin-8-oxy-malonate, diallyl 5-chloro-quinolin-8-oxy-malonate, diethyl 5-chloro-quinolin-8-oxy-malonate, 2-(4-carboxy-chroman-4-yl)-acetic acid, 3,3'-dimethyl-4-methoxy-benzophenone, 1-bromo-4-chloromethylsulphonyl-benzene, N-(2-methoxy-benzoyl)-4-[(methylamino-carbonyl)-amino]-benzenesulphonamide, N-(2-methoxy-5-methyl-benzoyl)-4, (cyclopropylaminocarbonyl)-benzene-sulphonamide, N-cyclopropyl-4-[(2-methoxy-5-methyl-benzoyl)-amino-sulphonyl]benzamide, "active compounds of group 3")

excluding mixtures of flucarbazone or flucarbazone-sodium with cinidon-ethyl.

2. A method for controlling undesirable plants comprising the step of allowing a composition according to claim 1 to act on the undesirable plants and/or their habitat.

3. A process for preparing a herbicidal composition, comprising mixing a composition according to claim 1 with one or more surfactants and/or extenders.

4. A composition according to claim 1 wherein the compound which improves crop plant compatibility (component (c)) is selected from the group of active compounds consisting of:

1-methyl-hexyl 5-chloro-quinolin-8-oxy-acetate (cloquintocet-mexyl) and diethyl 1-(2,4-dichlorophenyl)-4,5-dihydro-5-methyl-1H-pyrazole-3,5-dicarboxylate (mefenpyr-diethyl).

5. A composition according to claim 1 wherein from 0.01 to 1000 parts by weight of the active compound(s) from the second group of herbicides (component (b)) are used per part by weight of active compound of the formula (I).

6. A composition according to claim 1 wherein from 0.001 to 1000 parts by weight of the active compound which improves crop plant compatibility (component (c)) is used per part by weight of active compound of the formula (I) or its mixtures with active compounds from the second group of herbicides (component (b)).

* * * * *